(12) United States Patent
Robinson et al.

(10) Patent No.: US 7,157,245 B2
(45) Date of Patent: *Jan. 2, 2007

(54) NEISSERIAL VACCINE COMPOSITIONS AND METHODS

(75) Inventors: Andrew Robinson, Salisbury (GB); Andrew Richard Gorringe, Salisbury (GB); Michael John Hudson, Salisbury (GB); Philippa Bracegirdle, Salisbury (GB); John Simon Kroll, Oxford (GB); Paul Richard Langford, Oxford (GB); Steven Anthony Rochford Webb, Sublaco (AU); Keith Cartwright, Brobury (GB); Cliona Anne O'Dwyer, Furbo (IE); Karen Margaret Reddin, Salisbury (GB)

(73) Assignee: Health Protection Agency, Salisbury Wiltshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/942,583

(22) Filed: Aug. 31, 2001

(65) Prior Publication Data

US 2003/0026809 A1 Feb. 6, 2003

Related U.S. Application Data

(63) Continuation-in-part of application No. PCT/GB00/00624, filed on Feb. 22, 2001.

(30) Foreign Application Priority Data

Feb. 22, 1999 (GB) ................................ 9904028.9
Sep. 23, 1999 (GB) ................................ 9922561.7

(51) Int. Cl.
C12P 21/06 (2006.01)
C12N 15/09 (2006.01)
C12N 15/63 (2006.01)
C12N 15/00 (2006.01)
C12N 1/12 (2006.01)
A61K 38/00 (2006.01)
A61K 39/00 (2006.01)

(52) U.S. Cl. .................. 435/69.1; 435/69.7; 435/69.3; 435/71.1; 435/71.2; 435/71.3; 435/320.1; 435/252.1; 424/184.1; 514/2

(58) Field of Classification Search ............... 435/69.1, 435/69.7, 69.3, 71.1; 424/234.1, 235.1, 249.1, 424/250.1
See application file for complete search history.

(56) References Cited

U.S. PATENT DOCUMENTS

| 5,470,740 | A | * | 11/1995 | Longo et al. ......... 435/252.33 |
| 5,980,912 | A | | 11/1999 | Podolski et al. |
| 6,013,267 | A | | 1/2000 | Blake et al. ............. 424/249.1 |
| 6,413,768 | B1 | * | 7/2002 | Galen ........................ 435/320.1 |
| 6,703,233 | B1 | * | 3/2004 | Galen ........................ 435/252.3 |
| 6,737,521 | B1 | * | 5/2004 | Fischetti et al. ............ 536/23.4 |
| 2003/0021812 | A1 | * | 1/2003 | Robinson et al. ......... 424/249.1 |
| 2003/0026809 | A1 | * | 2/2003 | Robinson et al. ......... 424/190.1 |
| 2003/0215469 | A1 | * | 11/2003 | Robinson et al. ........ 424/250.1 |
| 2005/0013831 | A1 | * | 1/2005 | Foster et al. ............. 424/203.1 |

FOREIGN PATENT DOCUMENTS

| EP | 1297844 A2 | * | 4/2003 |
| WO | WO 96/29412 | | 9/1996 |
| WO | WO99/61620 | * | 12/1999 |
| WO | WO 03/051379 A1 | * | 6/2003 |

OTHER PUBLICATIONS

Moe etal, Infection and Immunity 70/11: 6021-6031, Nov. 2002.*
Martin etal, J. Exp. Med. 185/7: 1173-1183, Apr. 1997.*
Oliver et al, Infection and Immunity 70/7: 3621-3626, Jul. 2002.*
Parkhill et al, Nature 404: 502-506, Mar. 2002.*
Gómez etal, Vaccine, 16/17: 1633-1639, 1998.*
Ala'Aldeen etal, J. Med. Microbiology 44:237-43, 1996.*
Moe etal, Infection and Immunity 67/11: 5664-5675, Nov. 1999.*
Fusco etal, Exp. Opin. Invest. Drugs 7/2: 245-252, 1998.*
Moe etal, FEMS Immunology+Med. Microbiology 26:209-226, 1999.*
Pettit et al, Can. J. Microbiol 47:871-876, 2001.*
Grifantini etal, Ann. N.Y. Acad. Sci. 975: 202-216, 2002.*
Zhou et al, Molecular Microbiology 23/4: 799-812, 1997.*
Pannekock etal, Molecular Microbiology 15/2: 277-285, 1995.*
Linz et al, Molecular Microbiology 36/5: 1049-1058.*
Evans, Dissertation Abstracts International, 1989, vol. 50/08-B, p. 3315.*
Mielcarek et al, Advanced Drug Delivery Reviews, 2001, 51, 55-69.*
Sanchez et al, Vaccine, 2001, 19:3390-3398.*
O'Dwyer et al, Infection and Immunity, Nov. 2004, 72/11:6511-6518.*
Gorringe et al, Vaccine, 2005, 23:2210-2213.*
Bennett et al, Infection and Immunity, Apr. 2005, 73/4:2424-2432.*

(Continued)

Primary Examiner—Nita Minnifield
(74) Attorney, Agent, or Firm—Sterne, Kessler, Goldstein & Fox P.L.L.C.

(57) ABSTRACT

Methods and compositions for the treatment of microbial infection, and in particular meningococcal disease, comprise a commensal Neisseria or an extract of a commensal Neisseria. Further methods and compositions comprise commensal Neisseria which express genes from virulent strains of Neisseria and/or heterologous gene products from non-neisserial sources. Such compositions are used in vaccine preparations for the treatment of microbial infection.

10 Claims, 17 Drawing Sheets

OTHER PUBLICATIONS

Pollard et al, Vaccine, 2001, 19:1327-1346.*
Mukhopadhyay et al, Biotechnol. Appl. Biochem., 2005, 41:175-182.*
Jodar et al, Lancet, 2002, 359:1499-1508.*
Oftung et al, FEMS Immunology and Medical Microbiology, 1999, 26:75-82.*
Serruto et al, J. Biotechnology, 2004, 113:15-32.*
Locht, PSTT, Apr. 2000, 3/4:121-128.*
Humphries et al, Vaccine, 2004, 22:1564-1569.*
Medaglini et al, Vaccine, 1997, 15/(12/13):1330-1337.*
Ellis, Vaccine, 1999, 17:1596-1604.*
Aho et al, Infection and Immunity, Jul. 1997, 65/7:2613-2620.*
Tettelin et al, Science, 2000, 287:1809-1815.*
Gotschlich et al, J. Exp. Med., 1986, 164:868-881.*
Johnson et al, Infection and Immunity, Jul. 1996, 64/7:2627-2634.*
Goh et al, Antonie can Leeuwenhock et al, 2005, 87:205-213.*
Claassen et al, Vaccine, 14/10:1001-1008.*
Aho et al, Microbial Pathogenesis, 2000, 28:81-88.*
Toleman et al, Cellular Microbiology, 2001, 3/1:33-44.*
Troncoso et al, FEMS Microbioogy Letters, 2001, 199:171-176.*
van der Ley et al, Infection and Immunity, Aug. 1992, 60/8:3156-3161.*
van der Ley et al, Infection and Immunity, Oct. 1993, 61/10:4217-4224.*
Ferreiros et al, FEMS Microbiology Letters, 1991, 83:247-254.*

Cann, K. J. and Rogers, T.R., "Detection of antibodies to common antigens of pathogenic and commensal *Neisseria* species," *J. Med. Microbiol.* 30:23-30, The Pathological Society of Great Britain and Ireland (1989).

Gómez, J.A. et al., "Antigenicity, cross-reactivity and surface exposure of the *Neisseria meningitidis* 37 kDa protein (Fbp)," *Vaccine* 14:1340-1346, Elsevier Science Ltd (1996).

English abstract of Aoun, L. et al., "Human Antibody Response to the 70-KD Common Neisserial Antigen in Patients and Carriers of *Meningococci* or Non-Pathogenic *Neisseria*," *Annales de l'Institut Pasteur Microbiology* 139:203-212, Biosis Online accession No. PREV198886026860, XP-0021498186(1988).

Troncoso, G. et al., "Antigenic cross-reactivity between outer membrane proteins of *Neisseria meningitidis* and commensal *Neisseria* species," *FEMS Immunol. Med. Microbiol.* 27:103-109, Elsevier Science B.V. (Feb. 2000).

U.S. Appl. No. 10/185,769, filed Jul. 1, 2002, Robinson et al., mailed Nov. 28, 2003.

U.S. Appl. No. 10/185,769, filed Jul. 1, 2002, Robinson et al., mailed Jun. 18, 2004.

Hoehn, G.T. and Clark, V.G. "Distribution of a Protein Antigenically Related to the Major Anaerobically Induced Gonococcal Outer Membrane Protein among Other *Neisseria* Species," *Infection and Immunity* 58:3929-3933, American Society for Microbiology (1990).

* cited by examiner

Challenge dose $10^8$ CFU

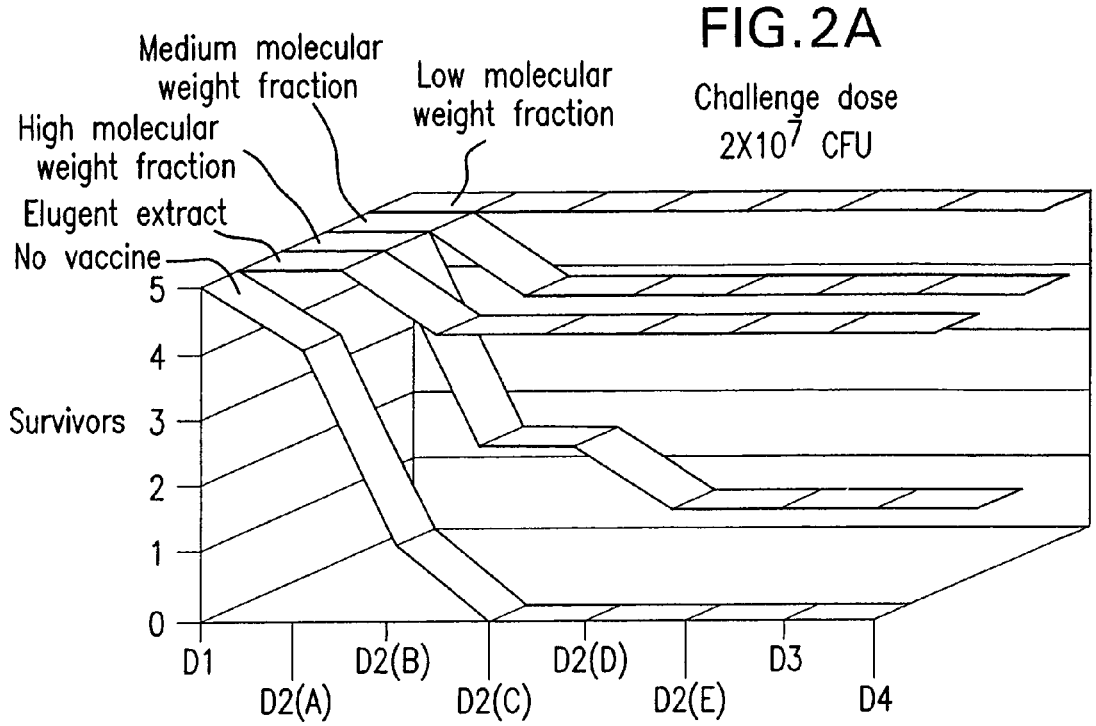
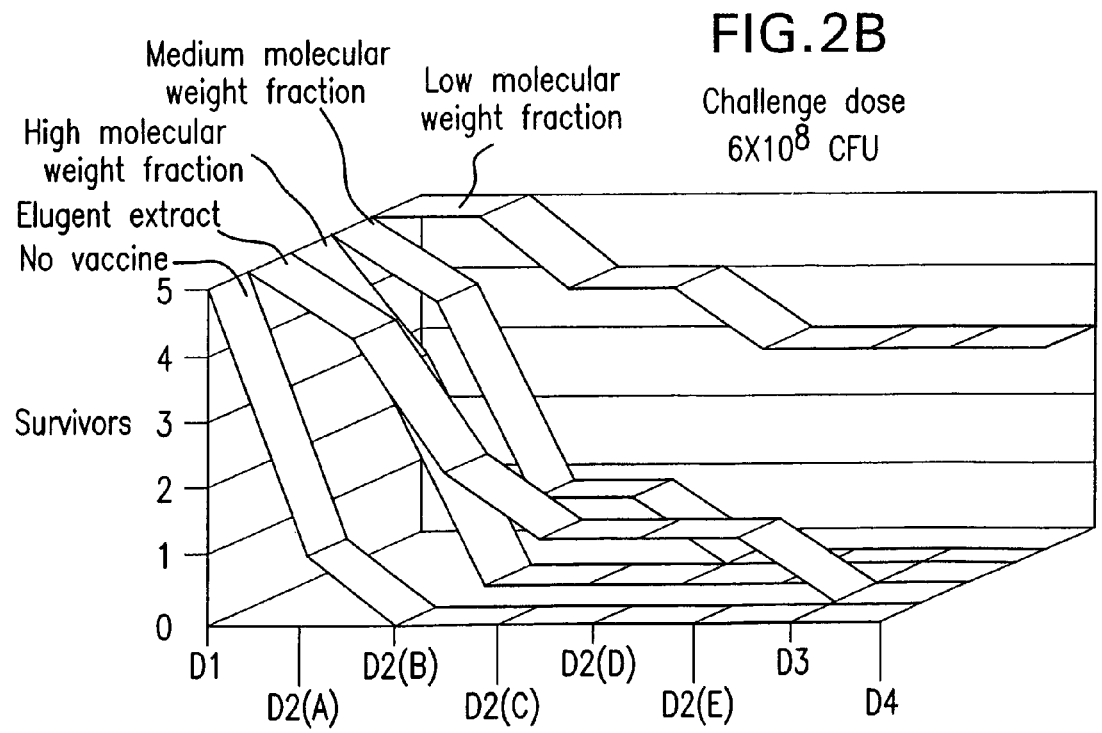

Fig. 11

NcoI - tgaccataaaggaaccaaaatatgaaaaaagcacttgccacactgattgccctcgctctcccggccgccgcactggcggaaggcgcatccttta
                       RBS     Start codon
cgtccaagccgatgccgcacacgcaaaagcctcaagctctttaggttctgccaaaggcttcagcccgcgcatctccgcaggctaccgcatcaacgacctccgcttcgccgt
cgattacacgcgctacaaaaactataaagccccatccaccgatttcaaactttacagcatcggcgcgtccgccatttacgacttcgacacccaatcgcccgtcaaaccgtatct
cggcgcgcgcttgagcctcaaccgcgcctccgtcgacttgggcggcagcgacagcttcagccaaacctccatcggcctcggcgtattgacgggcgtaagctatgccgtta
ccccgaatgtcgatttggatgccggctaccgctacaactacatcggcaaagtcaacactgtcaaaaacgtccgttccggcgaactgtccgtcggcgtgcgcgtcaaattctga
tatgcgcctt attctgcaaaccgccgagccttcggcggttttgttttct – PstI
                                Stop codon     Transcription terminator

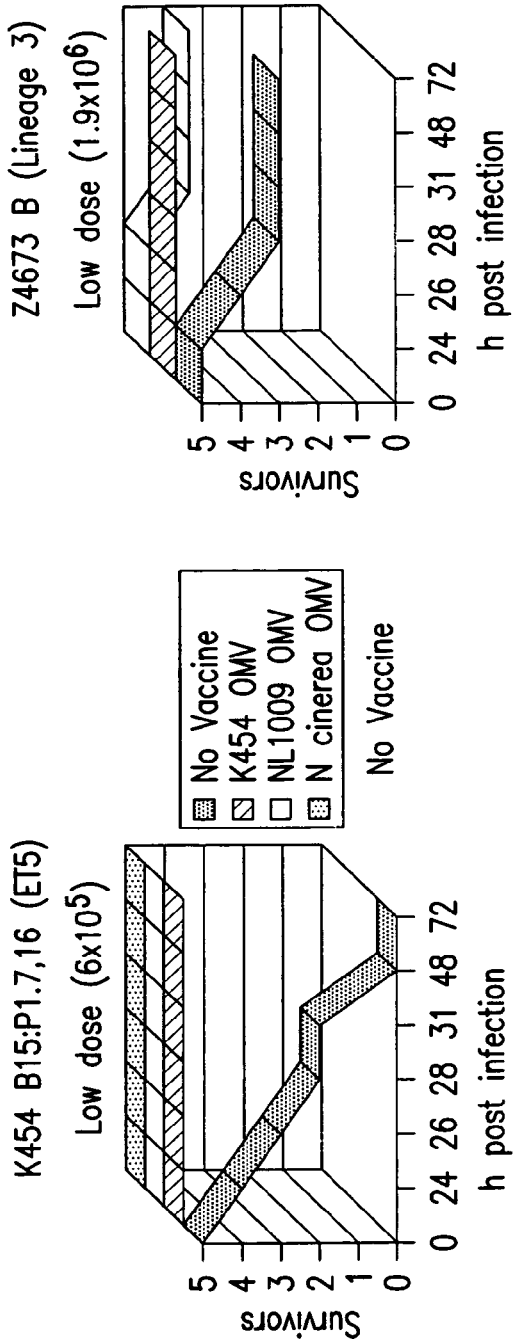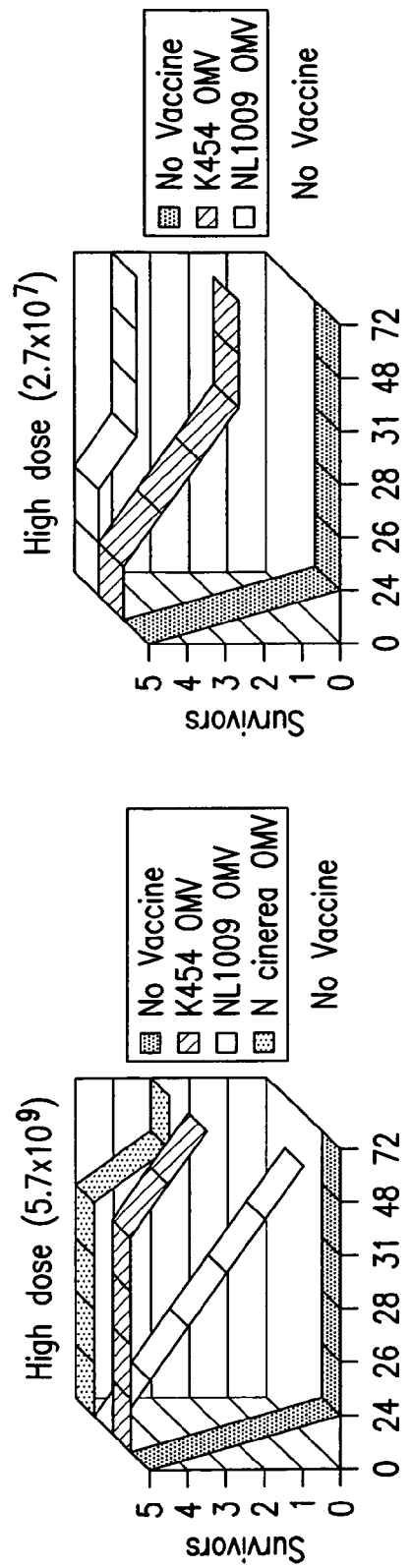
FIG. 12A  FIG. 12B  FIG. 12C  FIG. 12D

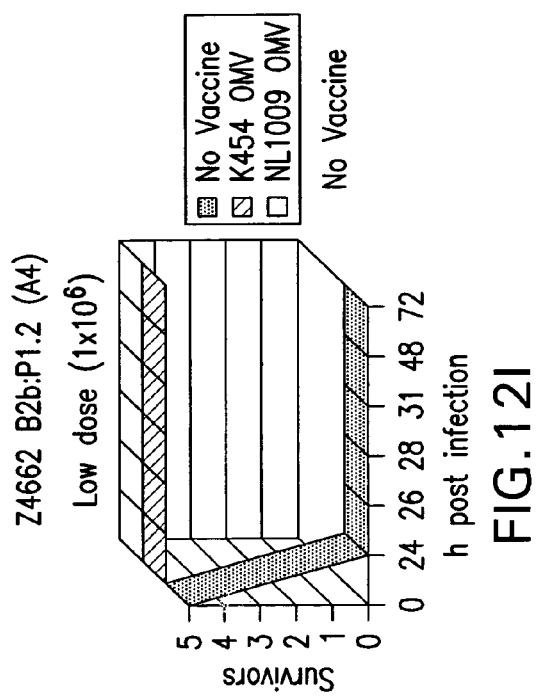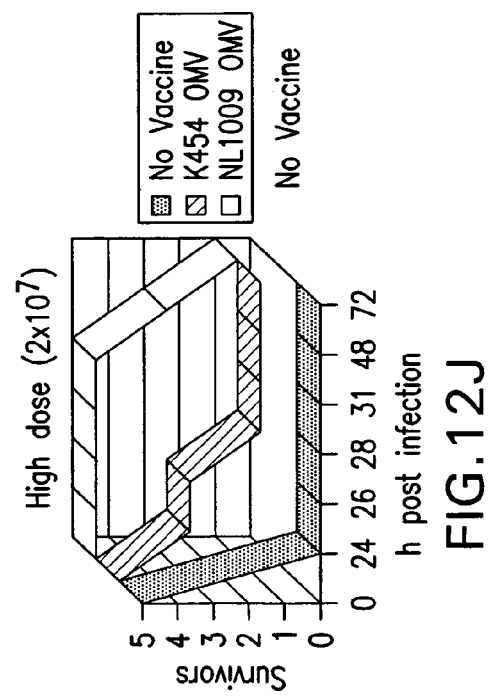

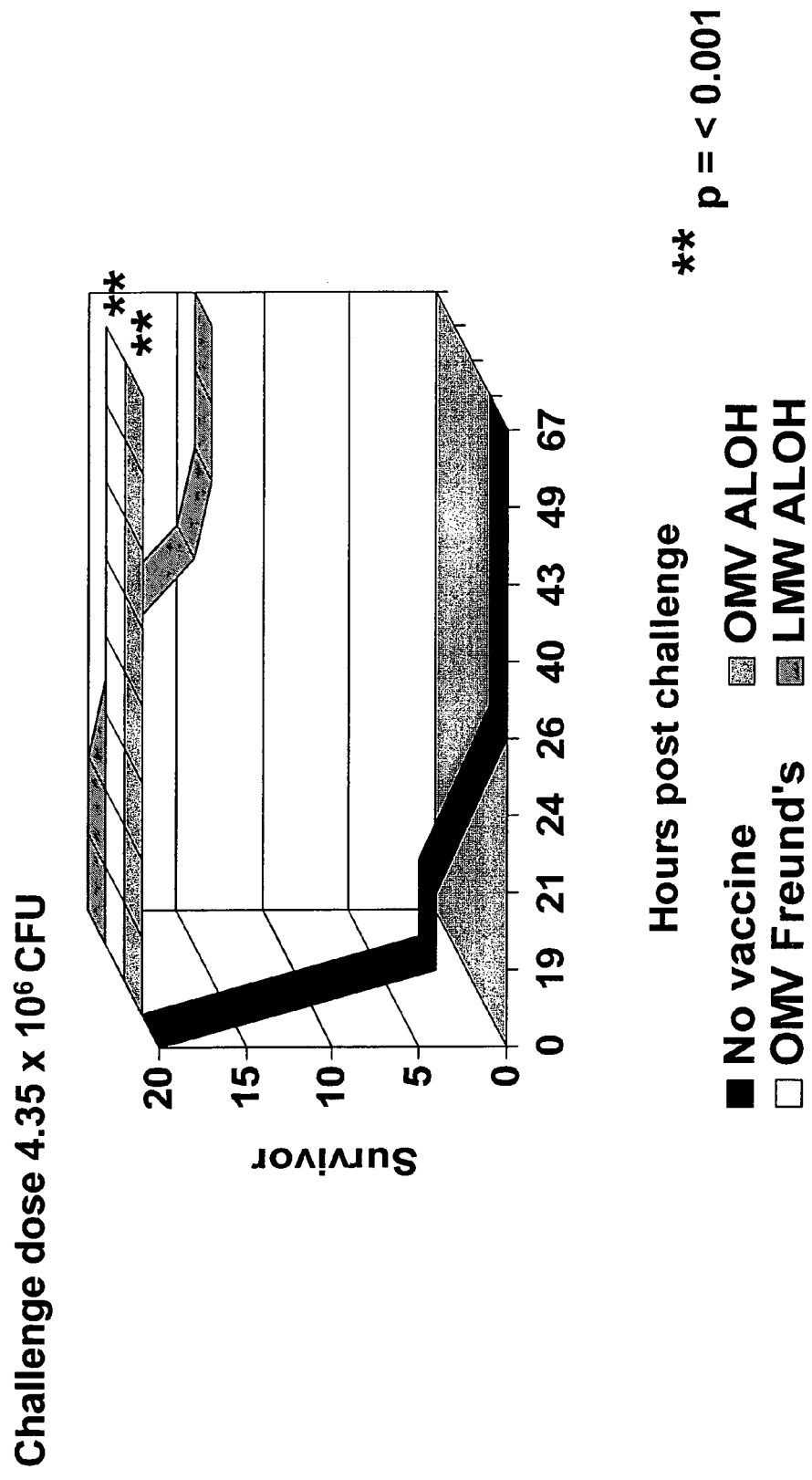
Fig. 14. *N. lactamica* OMVs with Freund's or alum adjuvant protect mice against serogroup B meningococcal challenge (isolate K454)

NEISSERIAL VACCINE COMPOSITIONS AND METHODS

The present application is a Continuation In Part of a U.S. National Phase PCT/GB00/00624 Application filed on Feb. 22, 2001 (International Filing Date of Feb. 22, 2000), and published in English on Aug. 31, 2000, the disclosure of which is incorporated herein by reference in its entirety.

The present invention relates to vaccines and methods for preparing vaccines that stimulate an immune response. In particular, the present invention relates to vaccines that provide broad spectrum protective immunity to microbial infection.

Infection by pathogenic organisms is one of the major causes of chronic and acute disease. In particular, infection resulting from microbial sources—such as bacteria, viruses and protozoans—continue to claim millions of lives worldwide. With microbial species increasingly becoming resistant to conventional antibiotics, it would be desirable to provide alternative and preferably prophylactic means of protecting against and fighting microbial infection.

Meningococcal meningitis is of particular importance as a worldwide health problem and in many countries the incidence of infection is increasing. *Neisseria meningitidis* (the meningococcus) is the organism that causes the disease and is also responsible for meningococcal septicaemia, which is associated with rapid onset and high mortality, with around 22% of cases proving fatal.

At present, vaccines directed at providing protective immunity against meningococcal disease provide only limited protection because of the many different strains of *N. meningitidis*. Vaccines based upon the serogroup antigens, the capsular polysaccharides, offer only short lived protection against infection and do not protect against many strains commonly found in North America and Europe. A further drawback of these vaccines is that they provide low levels of protection for children under the age of 2 years, one of the most vulnerable groups that are commonly susceptible to infection. Newer conjugate vaccines now in use in the UK will address some of these problems but will only be effective against the C serogroup of the meningococcus Gold et al. (Journal of Infectious Diseases, volume 137, no. 2, February 1978, pages 112–121) have reported that carriage of *N. lactamica* may assist in the development of natural immunity to *N. meningitidis* by induction of cross-reactive antibodies. This conclusion was based on the observation of cross-reacting antibodies having complement-dependent bactericidal activity produced in response to *N. lactamica* infection. However, Cann and Rogers (J. Med. Microbiol., volume 30, 1989, pages 23–30) detected antibodies to common antigens of pathogenic and commensal *Neisseria* species, but observed also that antibody to the same antigens was present in both bactericidal and non-bactericidal sera. Thus, it was not possible to identify any cross-reactive bactericidal antibodies.

Live attenuated vaccines for meningococcal disease have been suggested by Tang et al. (Vaccine 17, 1999, pages 114–117) in which a live, attenuated strain of *N. meningitidis* could be delivered mucosally. Tang also commented on the use of commensal bacteria to protect against infection by pathogenic bacteria, concluding that the cross-reactive epitopes that induce protection against meningococcal infection have not been defined, and therefore that use of genetically modified strains of *N. meningitidis* would be preferred.

It is desirable to provide a further vaccine that gives protective immunity to infection from *N. meningitidis*. It further is desirable to provide a vaccine that confers protective immunity to infants as well as adults and whose protection is long term. It may also be of advantage to provide a vaccine that protects against sub-clinical infection, i.e. where symptoms of meningococcal infection are not immediately apparent and the infected individual may act as a carrier of the pathogen. It would further be of advantage to protect against all or a wide range of strains of *N. meningitidis*. It is still further desirable to provide a vaccine against other neisserial infection, notably gonorrhoea.

It is an object of the present invention to provide compositions containing immunostimulating components, and vaccines based thereon, that meet or at least ameliorate the disadvantages in the art.

The present invention is based on the use of a commensal *Neisseria* in a vaccine against disease. Accordingly, a commensal species of *Neisseria* such as *N. lactamica* may be used as a live vaccine or a killed whole cell vaccine, or in a vaccine containing fractions of *N. lactamica*. It has surprisingly been demonstrated that mice immunised according to the present invention with *N. lactamica* killed whole cells and outer membrane preparations are protected from lethal intraperitoneal meningococcal challenge, and that vaccines composed of a detergent extract of *N. lactamica* cells or fractions of this, separated by preparative electrophoresis, also protect mice from lethal meningococcal challenge. These results have been obtained using mice and the mouse model used is regarded as predictive of corresponding immunogenic and vaccinating effects in humans.

Accordingly, a first aspect of the present invention provides an immunogenic composition, comprising a commensal *Neisseria* or an immunogenic component, extract or derivative thereof and a pharmaceutically acceptable carrier.

The composition of the invention is particularly suited to vaccination against infection of an animal. The term "infection" as used herein is intended to include the proliferation of a pathogenic organism within and/or on the tissues of a host organism. Such pathogenic organisms typically include bacteria, viruses, fungi and protozoans, although growth of any microbe within and/or on the tissues of an organism are considered to fall within the term "infection".

Commensal micro-organisms are those that can colonize a host organism without signs of disease. A number of different commensal *Neisseria* are suitable for use in the invention, and these commensal *Neisseria* may be selected from the group consisting of *N. lactamica, N. cinerea, N. elongata, N. flava, N. flavescens, N. polysaccharea, N. sicca, N. mucosa, N. perflava* and *N. subflava*. Different species of these commensal organisms are known to colonise the buccal or nasal areas or other mucosal surfaces and hence each species may be administered according to the known area of the body it normally colonises. Hence also, use of a composition of the invention may result in stimulation of production of protective antibodies de novo or if the individual has already been colonised to a certain extent may result in an enhancement of naturally-existing antibodies.

The "extract" or "component" is an extract or component that is immunogenic such that antibodies raised against the extract or component of a commensal *Neisseria* cross react with a pathogenic *Neisseria*, in particular *N. meningitidis*.

The term "derivative" is used to describe types and strains of commensal *Neisseria* that are modified or attenuated in some way so as to differ from the wild type species; for example, a vaccine composition comprising a recombinant commensal *Neisseria* that exhibits resistance to certain types of antibiotic compounds, which might advantageously be utilised in combination with such antibiotics in the treatment of infection.

It is an advantage of the invention that vaccination against neisserial diseases may thus be achieved using a non-pathogenic species of *Neisseria*, rendering the vaccination a safer procedure. Furthermore, the protection conferred surprisingly may not be restricted to a specific serotype, subtype or serogroup of the meningococcus but is of general protective efficacy.

A further advantage of the invention is that the commensal *Neisseria* that are the subject of the invention can not revert to virulent types. It is known in the vaccination field to use live, attenuated pathogens and this use carries the risk that the attenuated organism may revert to virulence. This risk is avoided by the present invention. Furthermore, *N. meningitidis* possesses many virulence factors the precise roles of which in pathogenesis are unknown and may possess hitherto unrecognised virulence factors. Therefore, an additional advantage of the invention is that a composition of the invention can be used with confidence in its level of safety.

The method of the invention is of application to vaccination against various infections, preferably but not only neisserial infections. In a specific embodiment of the invention, protection against meningococcal disease has been demonstrated. The invention is also of application to vaccination generally against neisserial infection, including gonorrhoeal infection, and also to infection from other pathogenic microbial organisms. The invention further provides for vaccination that is aimed at either stimulating or desensitizing the immune system.

The composition can specifically comprise killed commensal *Neisseria*, which may for example be obtained by heat or by suspending commensal *Neisseria* in a mixture of bactericidal agents such as thiomersal and formaldehyde.

The composition may also comprise live commensal *Neisseria*. As mentioned, it is optional but not usually required to use attenuated commensal *Neisseria* as these organisms are avirulent.

In an embodiment of the invention, an immunogenic component or extract of a commensal *Neisseria* is selected from an outer membrane vesicle preparation, an outer membrane preparation, lipooligosaccharide and a protein fraction.

The outer membrane preparation and protein fraction of, for example, *N. lactamica* can be obtained from *N. lactamica* cultured in the presence or absence of iron. The protein fraction of *N. lactamica* is conveniently obtained by suspending *N. lactamica* cells or membranes in the presence of detergent and incubating the suspension so as to extract proteins from the *N. lactamica*.

Alternatively, a number of other techniques are known for extraction of outer membrane components—such as protein fractions, lipooligosaccharides and lipopolysaccharides—from cell preparations and are suitable to obtain the commensal *Neisseria* immunogenic components or extracts of the invention. Examples of conventional techniques for this purpose include the use of variation in salt concentration, chaotropic agents, variation in pH (high or low), enzymic digestion and mechanical disruption.

A number of different fractions are suitable for use in vaccinating against meningococcal disease. Particularly suitable fractions are those of molecular weight less than 50 kDa, of molecular weight more than 40 kDa and less than 70 kDa, and of molecular weight more than 60 kDa.

In more specific embodiments of the invention there is provided a composition for eliciting an immune response and suitable for use in vaccinating an individual against neisserial infection, more specifically meningococcal disease, comprising an antigenic component or antigenic components having the properties:—
(a) molecular weight 50 kDa or lower;
(b) obtainable from *N. lactamica*; and
(c) antibodies to the component(s) obtained from *N. lactamica* cross-react with *N. meningitidis*.

In use of a composition containing such a component, extracted using detergent, all mice treated with this component survived a challenged dose of $2 \times 10^7$ CFU *N. meningitidis* and three out of five mice survived a higher challenge dose of $6 \times 10^8$ CFU.

Another specific embodiment of the invention lies in a composition for eliciting an immune response and suitable for use in vaccinating an individual against neisserial infection, more specifically meningococcal disease, comprising an antigenic component or antigenic components having the properties:—
(a) molecular weight at least 40 kDa and up to 70 kDa;
(b) obtainable from *N. lactamica*; and
(c) antibodies to the component(s) obtained from *N. lactamica* cross-react with *N. meningitidis*.

In use of such a component of the invention, obtained using a detergent extract of *N. lactamica*, four out of five mice treated with the component survived a challenge dose of $2 \times 10^7$ CFU *N. meningitidis* and mice receiving a higher challenge dose of $6 \times 10^8$ CFU survived longer than a control group.

A still further embodiment of the invention lies in a composition for eliciting an immune response and suitable for use in vaccinating an individual against neisserial infection, more specifically meningococcal disease, comprising an antigenic component or antigenic components having the properties:—
(a) molecular weight at least 60 kDa;
(b) obtainable from *N. lactamica*; and
(c) antibodies to the component(s) obtained from *N. lactamica* cross-react with *N. meningitidis*.

In use of such a component, obtained using a detergent extract, one out of five mice survived a challenge dose of $2 \times 10^7$ CFU *N. meningitidis* and, whilst all mice succumbed to a higher challenged dose of $6 \times 10^8$ CFU, their survival time was longer than a control group which did not receive the component.

In an example of the invention in use, described in more detail below, proteins in the size ranges of 25–35 kDa and 35–43 kDa, extracted from a commensal Neisseria, conferred a significant level of immune protection when administered to mice as a vaccine composition.

By way of example of a method of extracting an antigenic component of the invention, an extraction method comprises:—
(i) suspending *N.lactamica*, cells in an aqueous solution of detergent;
(ii) incubating the suspension so as to extract the antigenic component from the *N.lactamica*;
(iii) centrifuging the suspension to separate the suspension into a supernatant and a pellet; and
(iv) fractionating the antigenic component from the supernatant.

This specific method can be modified according to the extraction protocol selected by the user, for example by using high salt concentration in the initial step (i). In further embodiments of the invention the antigenic component is obtained using recombinant technology by expression of a *N. lactamica* sequence in a suitable host such as *E. coli*.

In a second aspect of the invention there is provided a composition for vaccination against neisserial infection comprising a commensal *Neisseria* or an immunogenic component, extract or derivative thereof and a pharmaceutically acceptable carrier, wherein the commensal *Neisseria* comprises and expresses a gene from a pathogenic *Neisseria*.

This aspect of the invention offers the benefit of use of a commensal organism to deliver and/or present to the recipient an antigen from a pathogenic *Neisseria*. The gene optionally encodes a surface antigen or a protein that is secreted, and may code for an antigen from, for example, *N. meningitidis* or *N. gonorrhoeae*. The commensal *Neisseria* can be live or killed.

In an embodiment of the second aspect of the invention there is provided a composition for vaccination against meningococcal disease comprising a commensal *Neisseria* and a pharmaceutically acceptable carrier, wherein the commensal *Neisseria* comprises and expresses a *N. meningitidis* gene.

The *N. meningitidis* gene may encode for example a transferrin binding protein, a superoxide dismutase (SOD) for example a Cu, Zn SOD, neisserial surface protein A ("NspA"), a porin or another outer membrane protein. Gene sequences for the majority of these antigens are known in the literature. Kroll et al. in Microbiology 141 (Pt 9), 2271–2279 (1995) describe the sequence of Cu, Zn-SOD. Martin et al. in J Exp Med, Apr. 7, 1997, 185(7), pp 1173–1183 describe the sequence of NspA from *N. meningitidis*.

The invention also provides a pharmaceutical composition comprising a composition according to the first or second aspect of the invention plus a pharmaceutically acceptable carrier.

In a third aspect, the invention provides a method of vaccination against neisserial infection, comprising administering an effective amount of a composition according to the first and second aspects of the invention.

In use of an embodiment of the invention described in an example below, there is provided a method of vaccination against meningococcal disease, comprising administering an effective amount of a composition according to the first and second aspects of the invention.

In a fourth aspect of the invention there is provided a strain of a commensal *Neisseria*, such as *N. lactamica*, genetically modified so as to express a gene from a pathogenic *Neisseria*. The *N.meningitidis* gene may for example code for a protein selected from a transferrin binding protein, a SOD for example a Cu, Zn-SOD, NspA, a porin or another outer membrane protein.

The invention further provides, in a fifth aspect a method of extracting a protein for incorporation in a composition suitable for vaccinating against meningococcal disease, comprising:—
(i) suspending commensal *Neisseria*, for example *N.lactamica*, cells in the presence of detergent; and
(ii) incubating the suspension so as to extract a protein fraction from the cells.

The protein fraction can suitably be of molecular weight 50 kDa or lower, at least 40 kDa and up to 90 kDa or at least 80 kDa.

The composition may be combined with a pharmaceutically acceptable carrier—for example the adjuvant alum although any carrier suitable for oral, intravenous, subcutaneous, intraperitoneal intramuscular, intradermal or any other route of administration is suitable—to produce a pharmaceutical composition for treatment of meningococcal disease. Commensal *Neisseria* that are buccal colonizers can be administered in a mouthwash and nasal colonizers in a nasal spray.

Transferrin binding proteins are known to be located on the outer membranes of a number of Gram negative bacteria such as *N. meningitidis*. Formulations of the composition of the present invention with conventional carriers or adjuvants and optionally further supplemented by one or more antigens from *Neisseria* species, optionally recombinantly produced, for example, Cu—Zn SOD, the 22 kD NspA, porins, gonorrhoeal antigens or transferrin binding proteins provide a composition for treatment of infection by these bacteria.

In the present invention, the term "transferrin binding protein" or "Tbp" refers to a protein which either alone binds to transferrin or can be part of a complex of proteins that binds transferrin. The term also embraces fragments, variants and derivatives of such a protein provided that antibodies raised against the fragment, variant or derivative bind the protein. Thus, TbpA and TbpB either dissociated or associated into a complex are considered to be Tbp. Moreover, mutants, fusion proteins or fragments of either TbpA or B or other derivatives of the TbpA+B complex with a common antigenic identity are also considered to be represented by the term Tbp in the present invention.

A live vaccine according to the present invention may be administered parenterally or to the mucosa for example via intranasal or oral inoculation. A killed bacteria, OMV or subunit vaccine may also be given by this route, or formulated for oral delivery. A subunit vaccine is conveniently administered via the parenteral route. Different commensal *Neisseria* and different strains of *N. lactamica* from those tested in specific embodiments of the invention exist, and the invention is of application also to those other strains.

A sixth aspect of the invention provides a composition comprising an antibody, wherein the antibody binds to a commensal *Neisseria* of the first or second aspects of the invention or an immunogenic component or extract thereof. In use, the antibody can be formulated into a pharmaceutical composition for treatment of neisserial infection, such as meningococcal disease or infection caused by other *Neisseria*.

An antibody according to this aspect of the invention can be obtained following standard techniques, for example by inoculating an animal with the commensal *Neisseria* or an immunogenic component or extract thereof and thereafter isolating antibodies that bind to the commensal *Neisseria* or the immunogenic component or extract thereof.

A further aspect of the invention provides for a composition comprising a commensal *Neisseria*, or an immunogenic component, extract or derivative thereof, wherein said *Neisseria* comprises a heterologous gene product.

Heterologous gene products of the invention typically include peptides, proteins and antisense sequences that are coded for by a gene sequence that is not native to the commensal *Neisseria*. Typical heterologous gene products of the invention include, for example, bacterial proteins, viral proteins or surface peptides, antigens and antibodies and fragments thereof. The heterologous gene product of the invention may also be any antigen found in a pathogenic organism.

In an embodiment of the invention, the composition comprises a commensal *Neisseria* into which has been transformed an expression vector containing a gene sequence encoding a heterologous gene product. Specific proteins suitable for use in the invention typically include:—

Viral proteins—such as hepatitis B virus surface antigen; rabies virus glycoprotein G; herpes simplex virus glycoprotein D; Epstein-Barr virus glycoprotein; influenza virus glycoprotein; vesicular stomatitis virus nucleoprotein; human respiratory syncytial virus glycoprotein G; human immunodeficiency virus (HIV) envelope; rotavirus subunits; measles virus subunits; and vaccinia virus subunits.

Bacterial proteins—such as *Bordetella pertussis* fimbrial subunits; *Bordetella pertussis* surface proteins; *Bacillus anthracis* subunits; *Escherichia coli* subunits; and *Yersinia pestis* subunits.

Protozoan proteins—such as *Plasmodium falciparum* proteins; trypanosome proteins; and Cryptosporidium proteins.

In a further embodiment the composition of the invention suitably provides for a commensal *Neisseria* that expresses a heterologous gene product which is immunostimulatory for treatment of non-infectious disease, for example allergy and cancer. In an example of the invention in use a commensal *Neisseria* that expresses peanut antigens is used to desensitize a patient with acute peanut allergy.

In a further example of the invention in use, described in more detail below, the expression vector pJSK422 is used to express green fluorescent protein, under the control of the groES/EL promoter, in the commensal *N. cinerea*.

The invention further provides for a commensal *Neisseria* that is transformed with an expression vector that comprises a signal sequence that directs the heterologous gene product to the outer membrane of the neisserial cell. Other signal sequences are also suitable for use in the invention, such as secretion signals or cellular subcompartment localisation signals e.g. periplasmic localisation signals.

Further aspects of the invention provide methods for preparing compositions. Such methods are suitable for preparing vaccine compositions that elicit protective immunity to microbial infection when administered to an animal.

An example of the invention in use, described in more detail below, provides for a method of preparing a composition comprising the steps of:

a) inserting a gene coding for a heterologous gene product into an expression vector;
b) transforming said expression vector into a commensal *Neisseria* so that said heterologous gene product is expressed in said *Neisseria*; and
c) combining the *Neisseria* of (b) with a pharmaceutically acceptable carrier.

A further example of the invention, provides for a method of preparing a composition comprising the steps of:

a) inserting a gene coding for a heterologous gene product into an expression vector;
b) transforming said expression vector into a commensal *Neisseria* so that said heterologous gene product is expressed in said *Neisseria*;
c) obtaining an immunogenic component or extract from the *Neisseria* of (b); and
d) combining the immunogenic component or extract of (c) with a pharmaceutically acceptable carrier.

In yet a further example of the invention in use is provided a method of preparing a composition comprising the steps of:

a) obtaining an immunogenic component or extract from a commensal *Neisseria*; and
b) combining the immunogenic component or extract of (a) with a heterologous gene product and a pharmaceutically acceptable carrier.

Thus, the invention provides for (a) methods and compositions in which an extract is taken from a commensal *Neisseria* that expresses a heterologous gene product, and (b) methods and compositions where an extract is obtained from a commensal *Neisseria* and the heterologous gene product expressed elsewhere (in another organism) is combined with this latter extract.

Further aspects of the invention provide for use of a commensal *Neisseria* in the manufacture of a medicament for treatment of neisserial infection, and for use of a commensal Neisseria, or an immunogenic component, extract or derivative thereof, wherein said *Neisseria* comprises a heterologous gene product, in the manufacture of a medicament for the treatment of infection or for immunostimulation in an animal.

Specific embodiments of the invention are discussed in more detail by means of the Examples described below. The results referred to in the Examples are illustrated by the accompanying drawings, in which:

FIGS. 2A and 2B show protection of mice against IP infection with *N.meningitidis* strain K454 by use of detergent and high, medium and low molecular weight extracts of *N.lactamica* cells—upper panel(FIG. 2A)=challenge by $2 \times 10^7$ CFU, lower panel(FIG. 2B)=challenge by $6 \times 10^8$ CFU;

Figure 10:
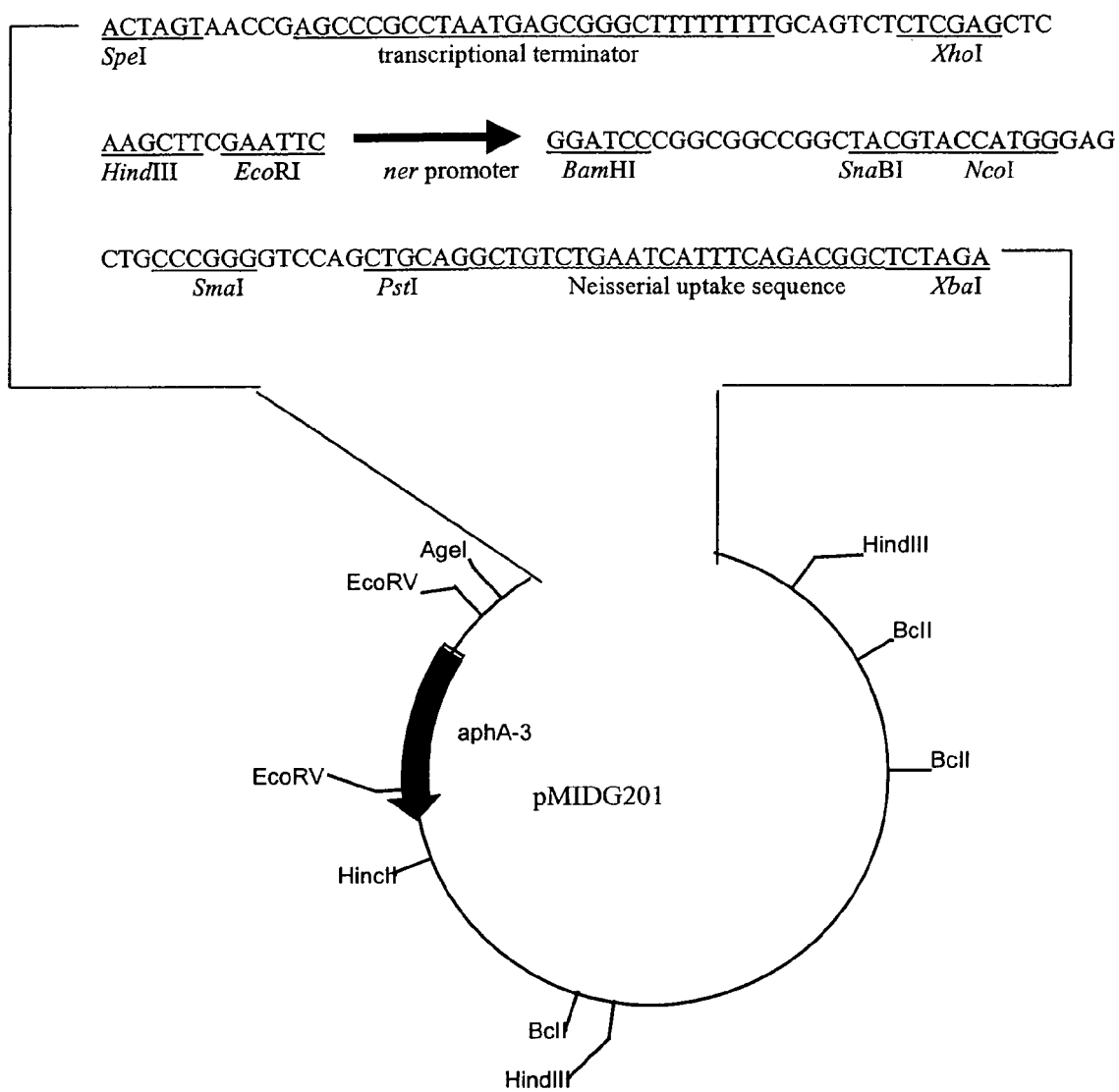
Figure 12G:
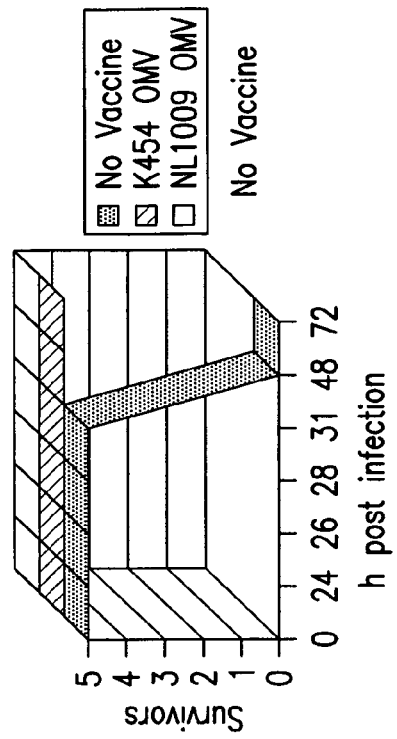
Figure 12H:
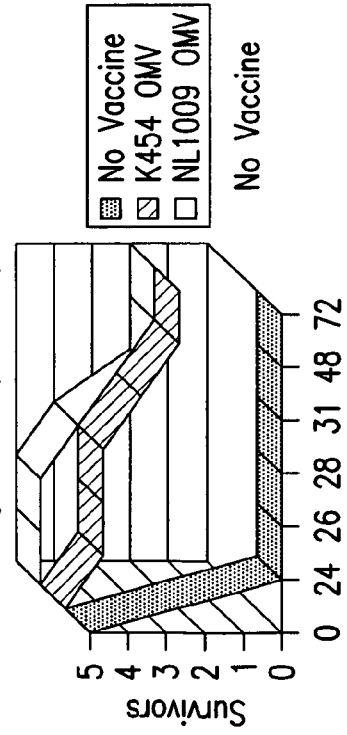
Figure 12E:
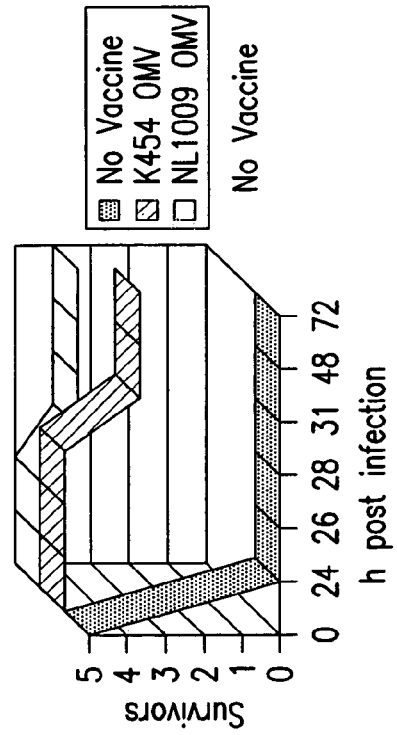
Figure 12F:
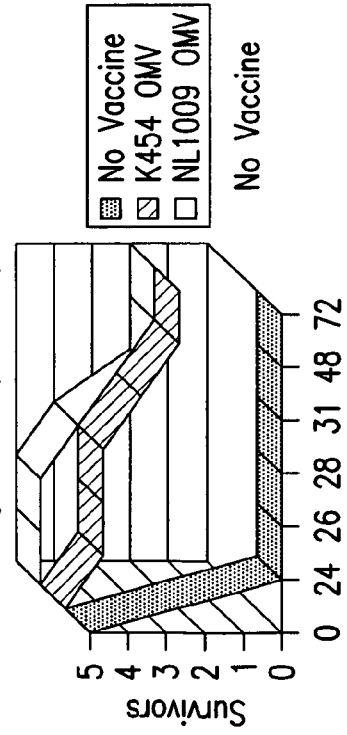
Figure 13A:
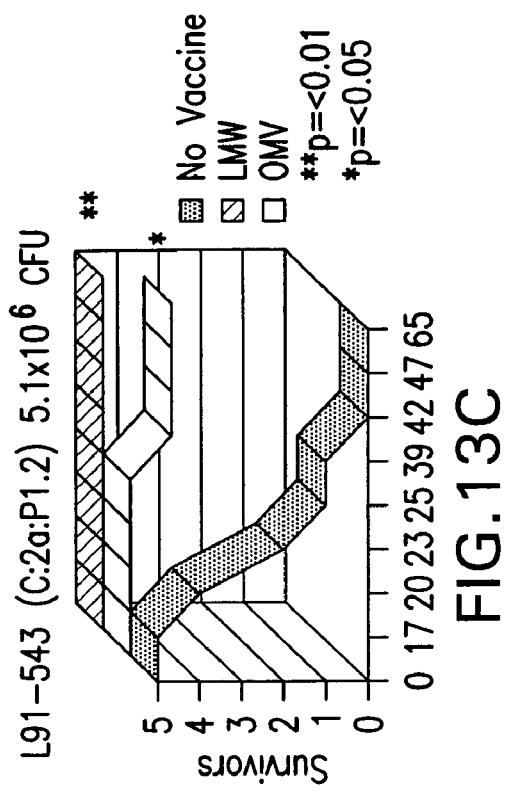
Figure 13B:
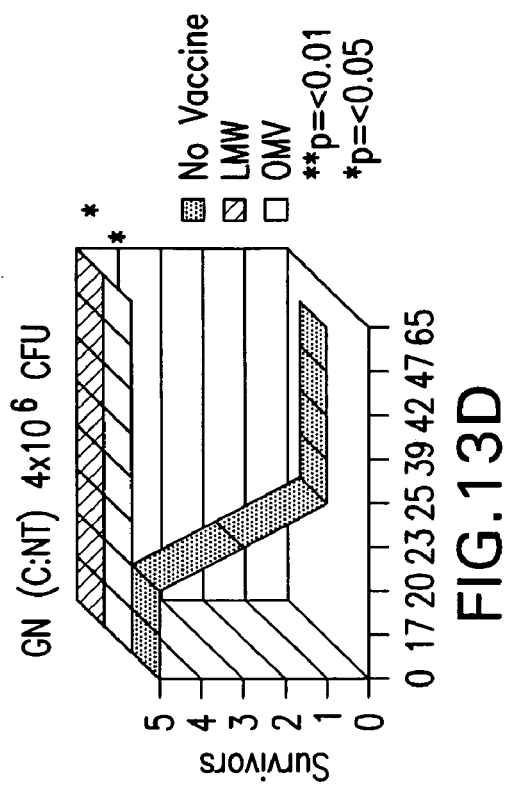
Figure 13C:
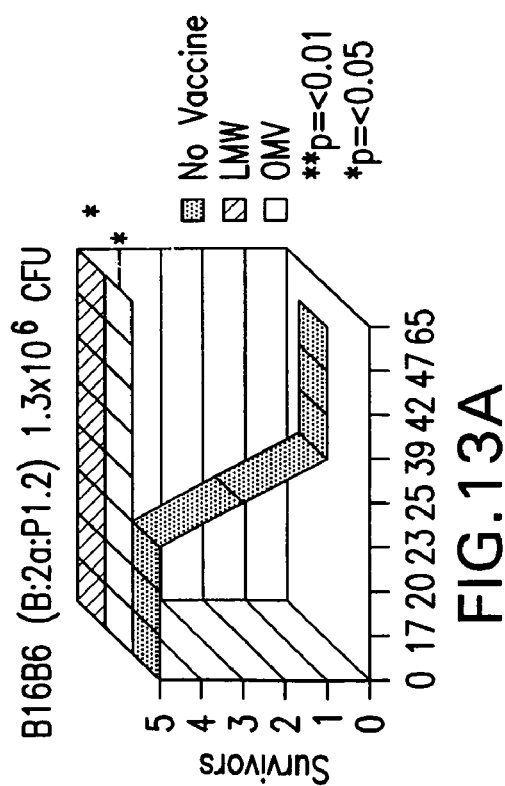
Figure 13D:
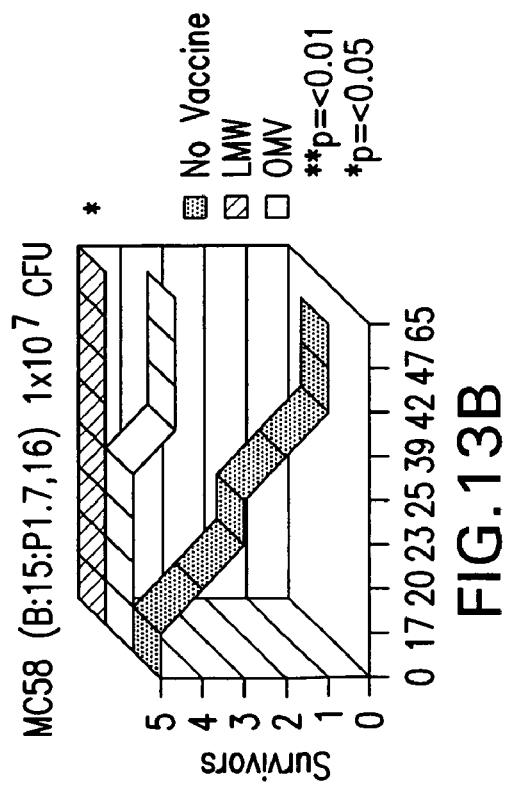

FIG. 10 shows a plasmid map of pMIDG201, containing a kanamycin cassette, a rho-independent upstream transcriptional terminator, (SEQ ID NO: 15), a multiple cloning site (SEQ ID NO: 16) and the ner promoter; and FIG. 11 shows Cassette I (SEQ ID NO: 12), containing a copy of nspA that can be cloned directly into the pMIDG200 plasmids, which has its own "native" upstream sequence, a RBS and a rho-independent terminator.

FIGS. 12A–12J show a comparision of the protection against meningococal challenge provided by *N. lactamica* OMVs, *N. meningitidis* OMVs (from strain K454) or *N. cinerea* OMVs. Protection against 5 different challenge strains from different clonal lineages is demonstrated.

FIGS. 13A–13D show protection against challenge by 4 different meningococcal strains provided by *N. lactamica* OMVs or the *N. lactamica* low molecular weight subtraction.

FIG. 14 shows that *N. lactamica* OMVs protect against meningococcal challenge in mice when administered in either Freund's or alum adjuvant. The low molecular weight subtraction also protects when given with alum adjuvant.

EXAMPLE 1

Preparation of Vaccine Containing Killed Whole Cells

*Neisseria lactamica* strain Y92-1009 was grown in Mueller Hinton broth (MHB) containing 5 µgml$^{-1}$ ethylenediamine-di(o-hydroxyphenylacetic acid) (EDDHA), incubated at 37° C. with shaking (140 rpm) for approximately 6 h.

Bacteria were then harvested by centrifugation and resuspended in phosphate buffered saline (PBS) containing 1% (v/v) formaldehyde and 0.1% (w/v) thiomersal, and left to stand overnight at 2–8° C. Killed cells were then resuspended in PBS to an OD$_{650}$ of 1.0 (equivalent to 2×10$^9$ CFUml$^{-1}$) and alhydrogel added to 25% (V/V), yielding a product suitable for subcutaneous administration.

This method is suitable also for other commensal Neisseria such as *N. cinerea, N. elongata, N. flava, N. flavescens, N. polysaccharea, N. sicca, N. mucosa, N. perflava* and *N. subflava*.

EXAMPLE 2

Preparation of Vaccine Containing *N. lactamica* Outer Membrane (OM) Preparations

*N. lactamica* strain Y92-1009 was grown in MHB with and without the addition of 5 µgml$^{-1}$ EDDHA overnight at 37° C. with shaking. Iron limited (with EDDHA) and iron replete cells were then treated separately. Bacteria from 1.5 litres were harvested by centrifugation and resuspended in 20 ml 200 mM Lithium acetate, 5 mM EDTA, pH 6.0 and incubated for 3 h at 37° C. with shaking. Bacteria were then passed 7 times through a 21 gauge needle and pelleted at 8000 g for 10 min.

The supernatant was recovered and membranes pelleted by centrifugation at 100,000 g for 1 h at 4° C. The membranes were then resuspended in 10 mM HEPES, pH 7.4, containing 0.1% (v/v) 10 mM PMSF, yielding OM-containing vaccinating preparations. The protein content of the OM vaccine preparations was determined using the bicinchoninic acid assay (Sigma, UK). OMs were diluted in sterile deionized water to give a protein concentration of 100 µgml$^{-1}$. This was then mixed with an equal volume of Freund's adjuvant, to give a final protein concentration of 50 µgml$^{-1}$, and emulsified thoroughly. Freund's complete adjuvant was used for the primary dose, and Freund's incomplete for subsequent boosts.

EXAMPLE 3

Preparation of Vaccine Containing Lipooligosaccharide (LOS)

Purification of LOS was carried out from *N. lactamica* strain Y92-1009 using the method of Gu, X—X and Tsai, C. M. (1991) Anal Biochem. 196; 311–318. Vaccine was prepared using Freund's adjuvant as above with LOS at a final concentration of 10 µgml$^{-1}$.

EXAMPLE 4

Vaccination and Challenge Schedule

Groups of 5 mice were vaccinated with each preparation as follows:—

| | |
|---|---|
| Prime:- | Day 0 |
| First boost:- | Day 21 |
| Second boost:- | Day 28 |

Mice vaccinated with killed cells of Example 1 received 0.5 ml subcutaneously, equivalent to 1×10$^9$ CFU. Mice vaccinated with OM of Example 2 and LOS of Example 3 received 0.2 ml subcutaneously; equivalent to 10 µg of protein and 2 µg of LOS.

Figure 1:
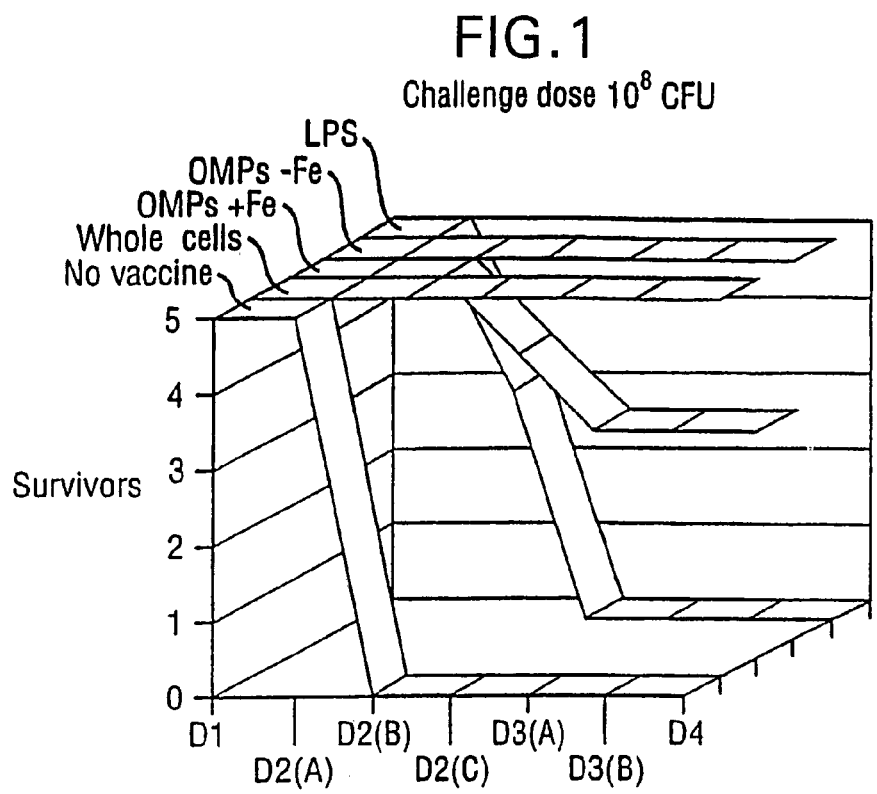
FIG. 1 shows protection of mice against intraperitoneal ("IP") infection with *N.meningitidis* strain K454 by use of *N.lactamica* whole cells and outer membrane fractions.

On day 35, mice were challenged by intraperitoneal injection with approximately 10$^8$ CFU *N. meningitidis* K454 made up in MHB containing transferrin at a final concentration of 20 mg/ml. The mice were then examined and the number of survivors noted and the results are shown in FIG. 1. After 4 days all 5 mice survived in the groups vaccinated with whole cells and OMPs (without iron) and 3 survived in the group vaccinated with OMPs (with iron). After 5 days all members of the control group and of the group vaccinated with LOS (marked LPS on the figure) had died.

EXAMPLE 5

Preparation of Vaccine Comprising *N. lactamica* Fractions

Brain heart infusion agar plates were inoculated with 50 µl of *N. lactamica* strain Y92-1009 and incubated overnight at 37° C., with 5% CO$_2$. This was used to inoculate a 100 ml MHB starter culture which was incubated with shaking at 37° C. for 6 h. Starter culture (15 ml) was added to each of 6×500 ml volumes of MHB. These were then incubated with shaking overnight at 37° C. and the conditions were made iron-limited by the addition of 5 µgml$^{-1}$ EDDHA. The cells were harvested by centrifugation and the supernatant discarded. The cells were washed with 100 ml PBS and then pelleted by centrifugation. Cell pellets were resuspended in PBS+0.3% (v/v) ELUGENT® (Calbiochem, 2 ml per g wet weight) and incubated with shaking at 37° C. for 20 min. The cells were then removed by centrifugation and the pellet discarded. EDTA and N-lauroyl sarcosine were then added to the supernatant to 10 mM and 0.5% (w/v) respectively.

An electrophoresis unit, the BioRad® Prep Cell, model 491 was then used to separate the proteins contained in the detergent extract. A 4 cm, 7% acrylamide native resolving gel was cast with a 2 cm stacking gel. 12 mg of protein in native sample buffer was electrophoresed using running buffer containing 0.1% (w/v) SDS, 0.025M Tris and 0.192M glycine at 40 mA and 400V until the dye front reached the bottom of the gel. 3 ml fractions of the eluted proteins were then collected. Once the fractions were collected they were pooled into groups consisting of proteins of molecular weight approximately less than 40 kDa, between 40 and 67 kDa and more than 67 kDa. The pooled proteins were concentrated by ammonium sulphate precipitation and dialysed against PBS. These were diluted in PBS to a protein concentration of 100 ug/ml and Freund's complete adjuvant was added at a ratio of 1:1 (v/v) or Freund's incomplete adjuvant for booster doses.

EXAMPLE 6

Vaccination and Challenge Schedule

Groups of 5 mice were vaccinated with each preparation as follows:—

| Prime:- | Day 0 |
| First boost:- | Day 21 |
| Second boost:- | Day 28 |

Mice were vaccinated with no vaccine (i.e. control group), ELUGENT® extract or high, medium or low molecular weight fraction. The mice receiving the protein fraction groups received 0.2 ml subcutaneously; equivalent to 10 µg of protein.

Figure 2C:
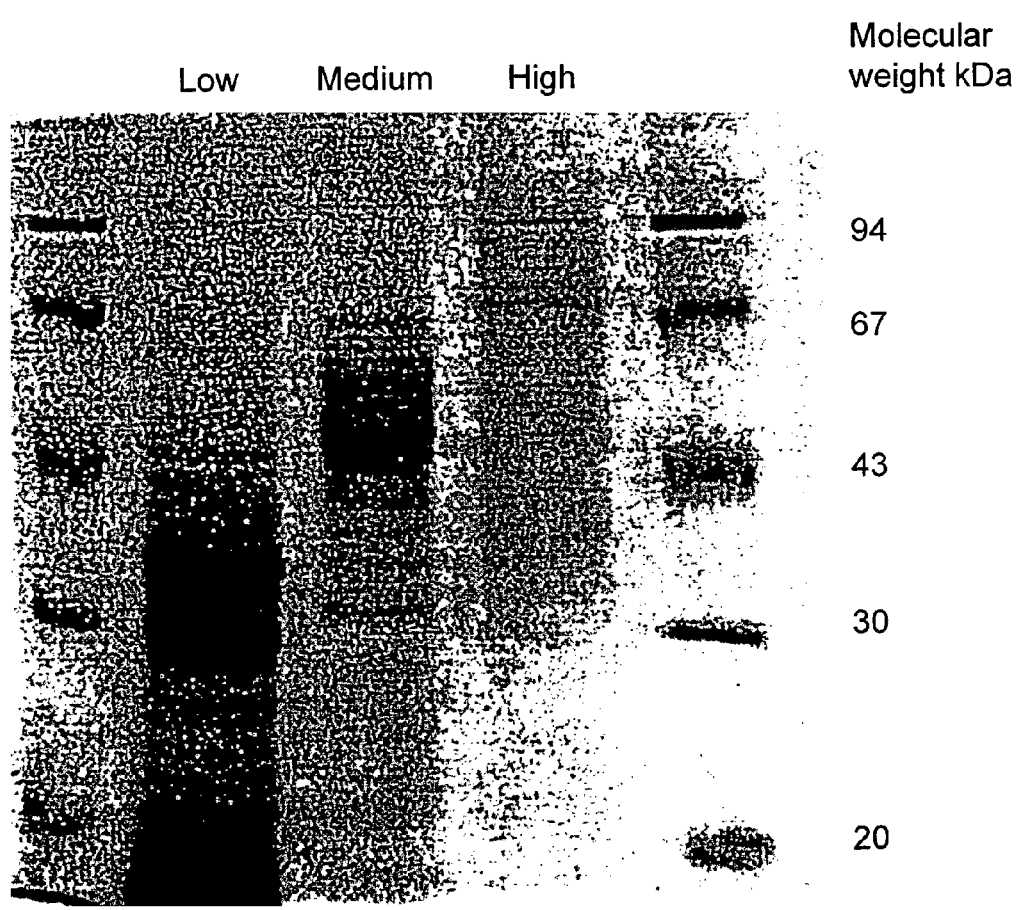
FIG. 2C shows the components of the high, medium and low molecular weight fractions of FIGS. 2A and 2B.

On day 35 mice were challenged by intraperitoneal injection with either approximately $2 \times 10^7$ or $6 \times 10^8$ CFU *N. meningitidis* K454 made up in MHB containing transferrin at a final concentration of 20 mg/ml. The mice were then examined over four days and the number of survivors noted, and the results are shown in FIG. 2A—upper panel $2 \times 10^7$ challenge and lower panel $6 \times 10^8$ challenge. The components of the high, medium and low molecular weight fractions are shown in FIG. 2B, after being run on SDS-PAGE gel.

EXAMPLE 7

Figure 3:
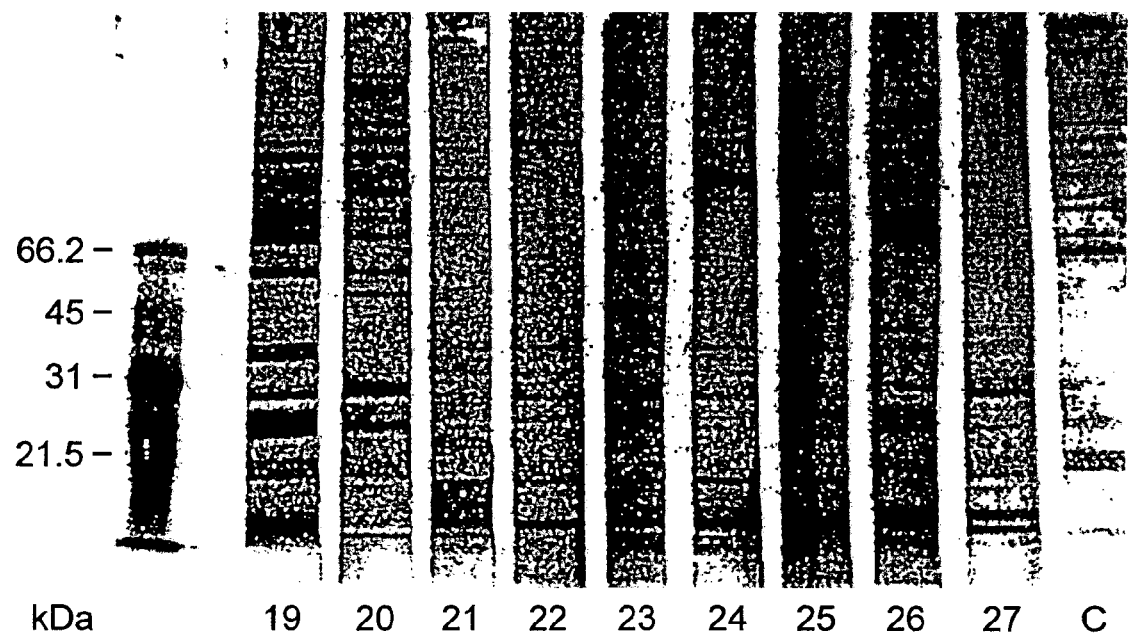
FIG. 3 shows an immunoblot illustrating cross-reaction of antibodies in sera from meningococcal disease patients with proteins from *N.lactamica* strain Y92-1009.

Samples of human sera following meningococcal disease were investigated and these showed that antibodies were produced which react with a range of *N. lactamica* proteins. The results of the immunoblot are shown in FIG. 3.

EXAMPLE 8

Figure 4:
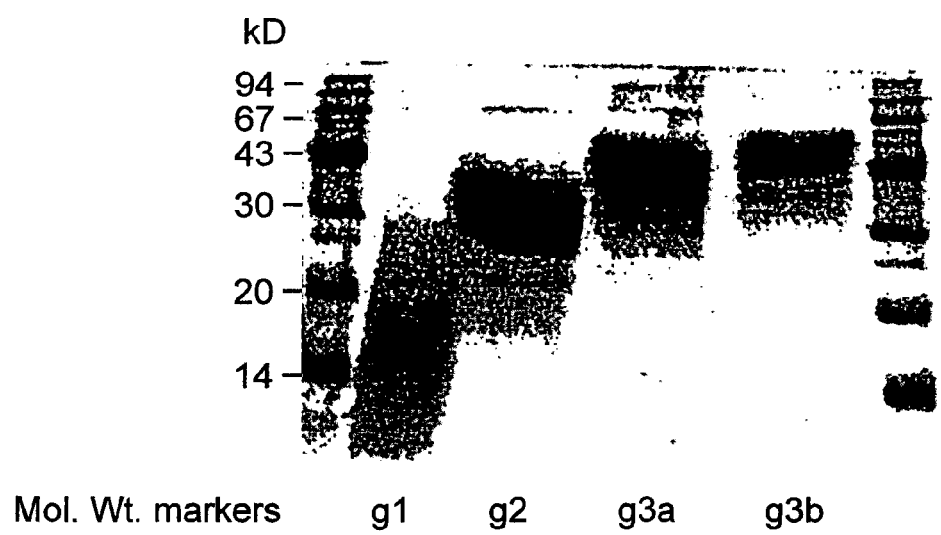
FIG. 4 shows a photograph of a gel on which subfractions of low molecular weight outer membrane protein extract have been run.

Due to the level of protection offered by the low molecular weight pool in Example 6 (see FIG. 2A), further separation of these proteins was carried out, according to the method of Example 5, to further characterise components responsible for protection. Proteins were pooled into three groups consisting of <25 kDa (g1), 25–35 kDa (g2) and 35–43 kDa (g3)(shown in FIG. 4). Determination of the levels of lipopolysaccharide (LPS) revealed high levels of LPS in fraction g1 [26 580 endotoxin units per ml (EUml$^{-1}$)], and considerably lower levels in the remaining fractions (9149 EUml$^{-1}$ in g2 and 9348 EUml$^{-1}$ in g3).

Figure 5A:
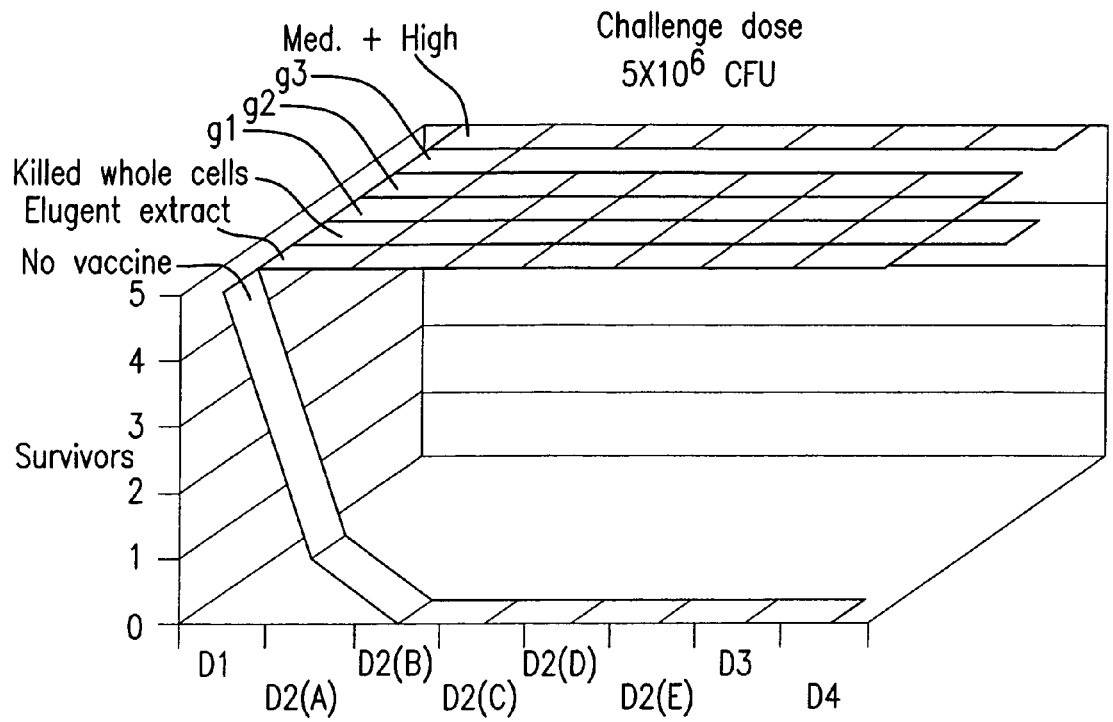
FIGS. 5A and 5B show protection of mice against IP infection with *N.meningitidis* strain K454 when immunised with low molecular weight subfractions—upper panel(FIG. 5A)=challenge by $5 \times 10^6$ CFU, lower panel(FIG. 5B)=challenge by $1 \times 10^8$ CFU.
Figure 5B:
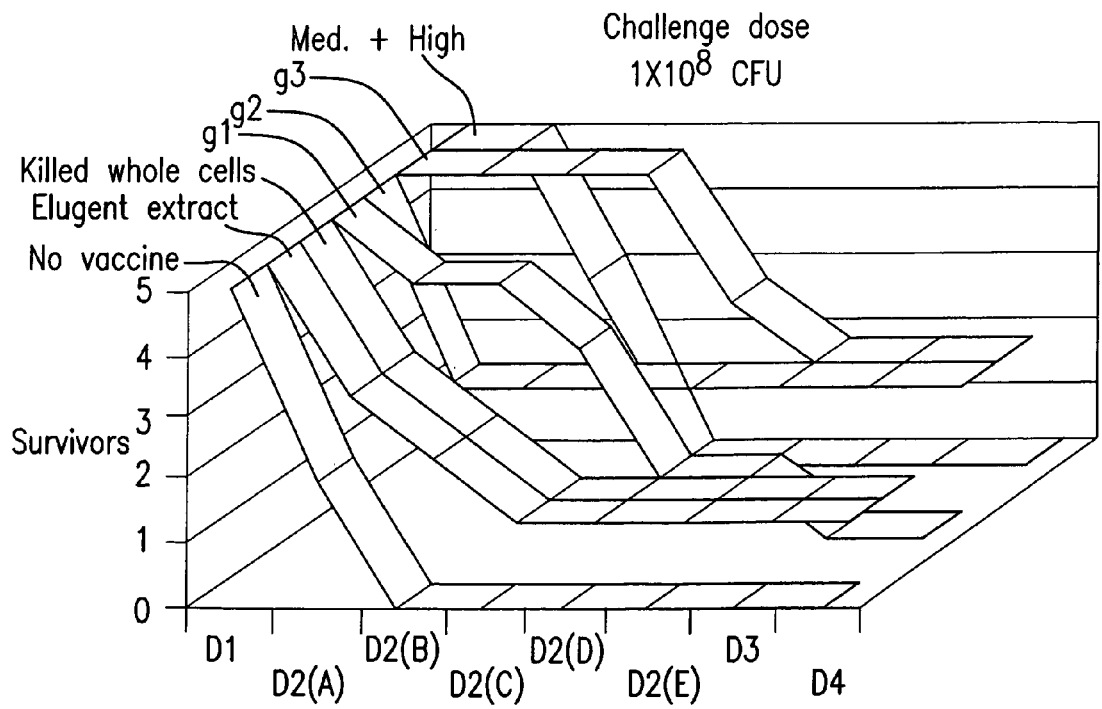
Figure 7:
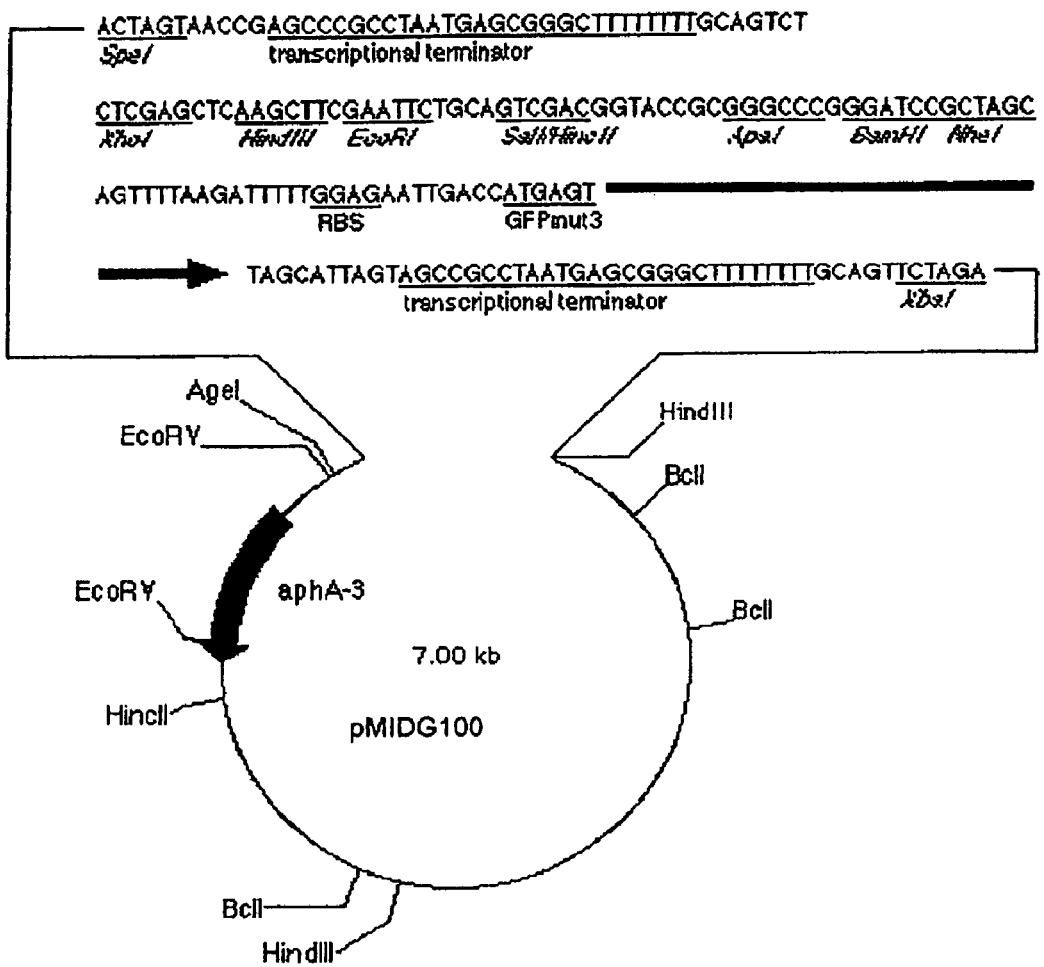
FIG. 7 is a map of Neisserial shuttle plasmid pMIDG100 containing a multiple cloning site (SEQ ID Nos: 13 and 14)
Figure 8A:
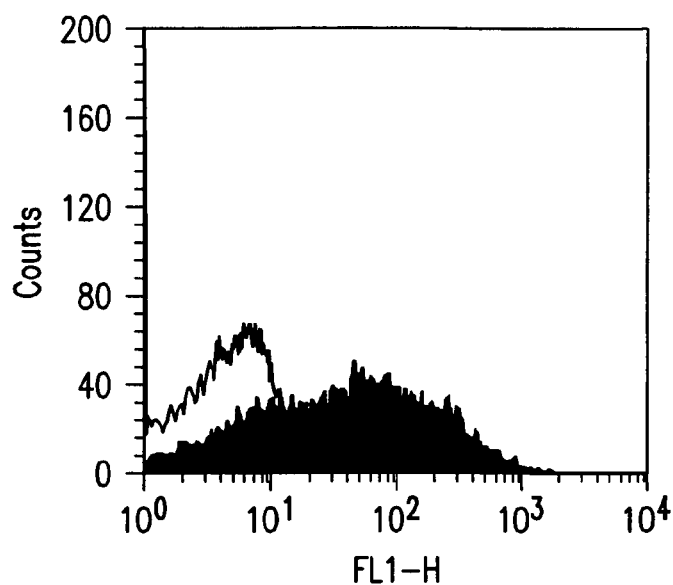
FIGS. 8A–8E show histograms comparing pMIDG100 (promoterless gfp) to pMIDG101 (gfp under the control of the ner promoter)
Figure 8B:
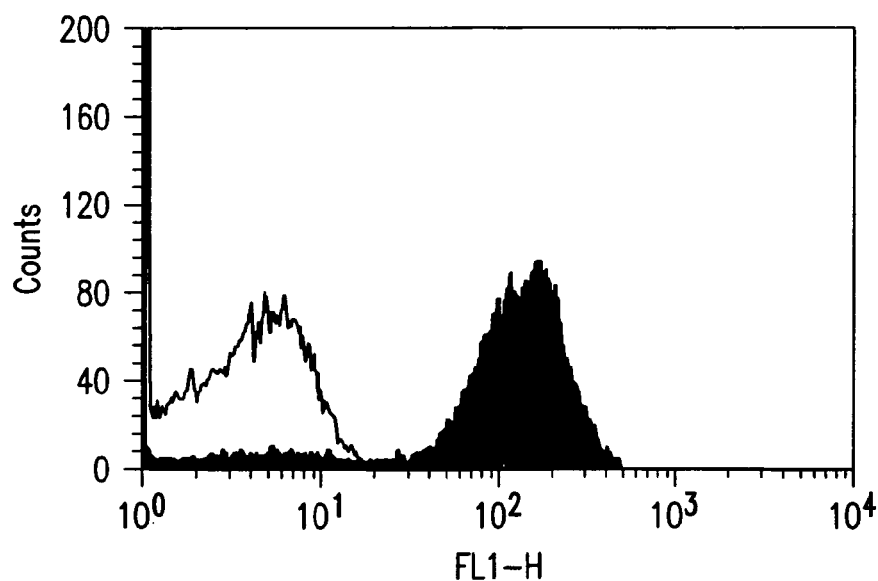
Figure 8C:
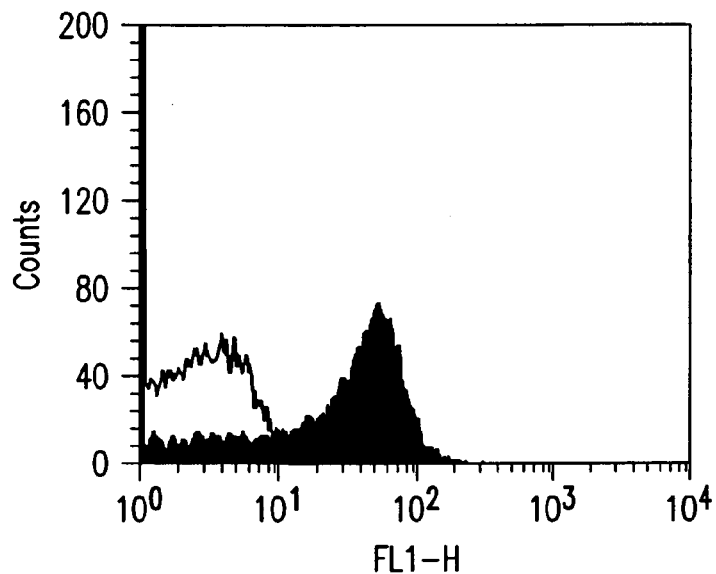
Figure 8D:
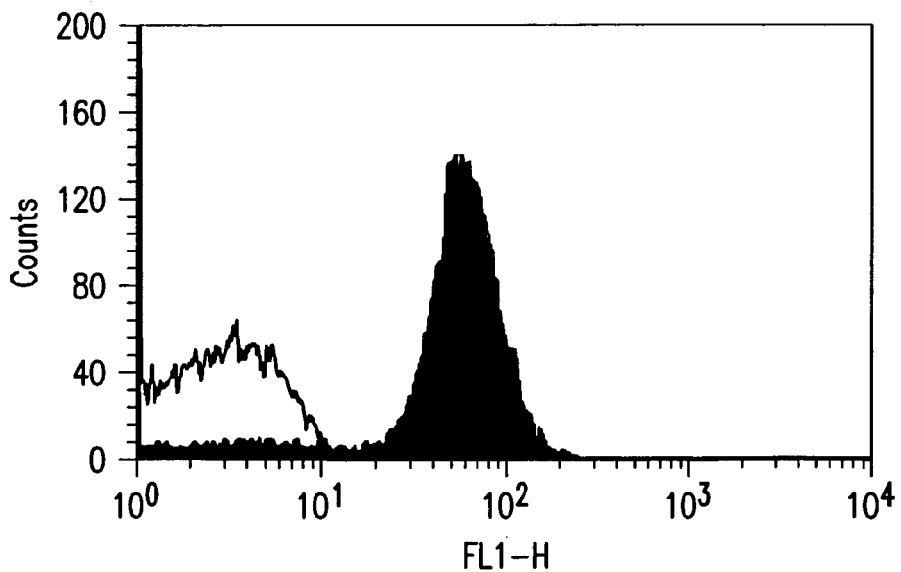
Figure 8E:
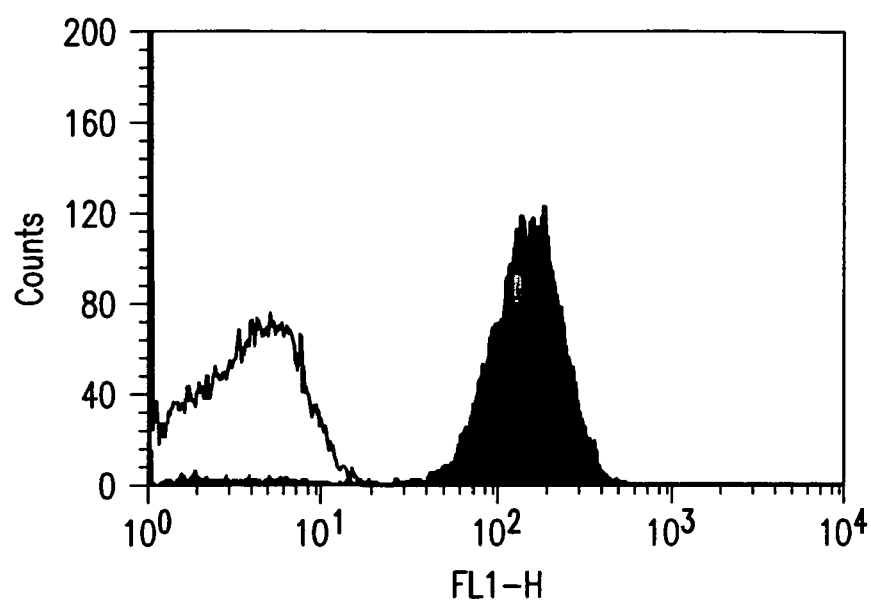

As in previous examples, groups of five mice were immunised, using a three dose schedule with one of the three groups of proteins described above, proteins >43 kDa and detergent extract of killed whole *N. lactamica* cells and killed whole *N. lactamica*. Animals were challenged with *N. meningitidis* serogroup B, strain K454, at a dose of $5 \times 10^6$ or $1 \times 10^8$ CFU, together with unimmunised controls. The number of survivors on each day post challenge is shown in FIG. 5.

All mice, apart from the control group and one mouse in group g3, survived the lower challenge dose; however, at the higher challenge dose the g2 and g3 protein groups (25–35 kDa and 35–43 kDa respectively) offered best protection.

EXAMPLE 9

Commensal *Neisseria* as a Vehicle for Recombinant Protein Expression

The gene encoding the measles virus nucleocapsid protein was cloned into the pMIDG101 vector and transformed into *E. coli* Top 10. Expression of the measles virus nucleocapsid protein was confirmed by western blotting probed with specific antiserum. This construct was then used to transform *N. cinerea* by conjugation. Expression of the measles virus nucleocapsid protein was placed under the control of the neisserial frpC promoter and expression at high levels was seen when the bacteria were grown under iron-limited growth conditions.

EXAMPLE 10

Expression of GFP in the Commensal *N. cinerea*

Using standard cloning techniques pMIDG100—containing the green fluorescent protein (GFP) gene of Aequorea Victoria—was modified by insertion of DNA containing the neisserial groES/EL promoter upstream of gfp. This created the pJSK422 plasmid, in which the GFP gene was under the control of the groES/EL promoter.

Figure 6:
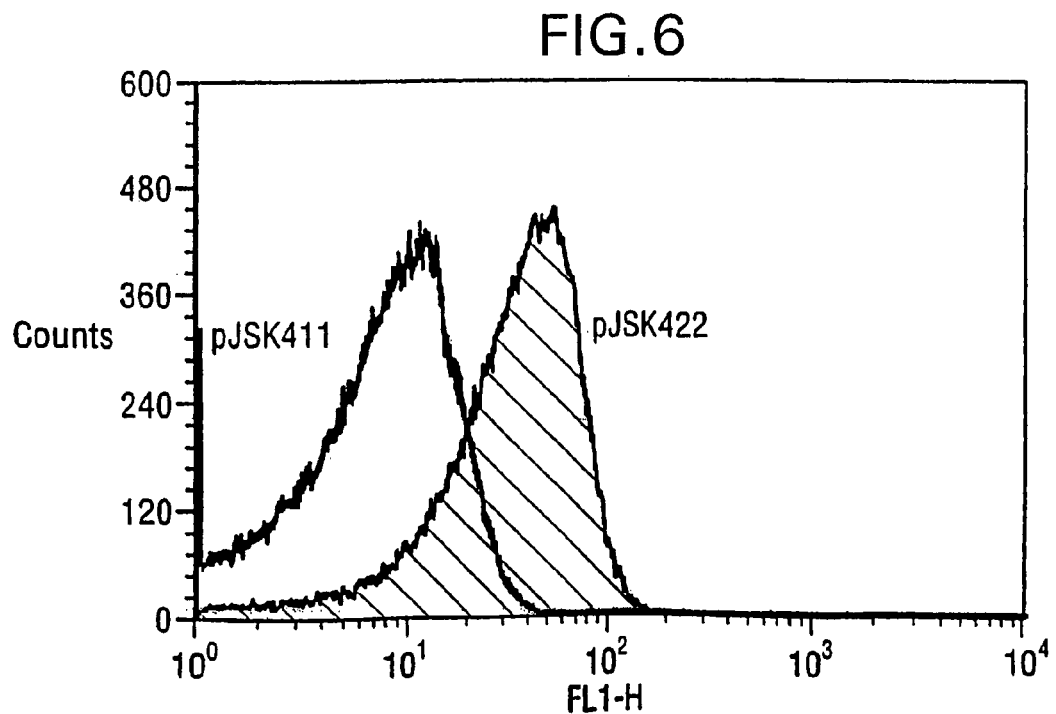
FIG. 6 shows a histogram comparing the fluorescence of *N. cinerea* NRL 32165 containing pJSK411 (promoterless GFP) (this vector is now known as pMIDG100)to pJSK422 (the pJSK411/pMIDG100 vector with a groEL/ES promoter).

*N. cinerea* was transformed via conjugation (see Example 9) either with the pJSK422 or pMIDG100 (negative control). The transformed cells were cultured under appropriate conditions. Fluorescence of the pJSK422 transformed cultures of *N. cinerea* were compared to that of the pMIDG100 transformed cultures. The results of the comparison are shown in FIG. 6. The histogram shows intensity of GFP fluorescence on the X axis and the number of cells fluorescing on the Y axis. It is clear that the level of fluorescence is higher in the *N.cinerea* transformed with pJSK422 than those transformed with pMIDG100, indicated by the peak shift to the right. This, demonstrates heterologous expression of the GFP gene in the commensal *N. cinerea*.

EXAMPLE 11

1: Expression of Foreign Antigens in Commensal *Neisseria*

1.1 Introduction

In this series of examples, we have expressed two foreign antigens, GFP and NspA, in a range of commensal *Neisseria*.

2: Materials and Methods 2.1 Bacterial Strains and Growth Conditions 2.1.1 Bacterial Strains Bacterial strains utilized during this work are described in the following tables. A very substantial collection of commensal *Neisseria* clinical isolates has been amassed through the generosity of various institutions in the UK and Dr Joan Knapp, CDC Atlanta.

| *E. coli* strains | Genotype/Phenotype | Reference |
|---|---|---|
| DH5α | F' φ80dlac Z M15 (lac ZYA-argF) U169 deo R recA1 endA1 hsdR17($r_k$- $m_k$+) phoA supE44 λ' thi-1 gyrA96 relA1 | (Hanahan, 1983) |

-continued

| E. coli strains | Genotype/Phenotype | Reference |
|---|---|---|
| S17-1 λpir | recA pro hsdR RP4-2-Tc::Mu-Km::Tn7 | (Simon R et al., 1983) |
| JM110 | F'[traD36 proA+ proB+ lacIq (lacZ M150 dam dcm supE44 hsdR17 thi leu thr rpsL lacY galK galT ara tonA tsx (lac-proAB) λ- | (Yanisch-Perron et al., 1985) |
| TOP10 | F−, mcrA (mrr-hsdRMS-mcrBC) φ80dlac Z M15 lacX74 deoR recA1 araD139 (ara-leu) 7697 ga/U ga/K rpsL(Str$^R$) endA1 nupG | (Hanahan, 1983) |

| N. meningitidis strains | Genotype/Phenotype | Reference |
|---|---|---|
| MC58 | serogroup B clinical isolate | (Virji et al., 1991) |

| N. lactamica strains | Source |
|---|---|
| Y921009 | CAMR |
| Y921011 | CAMR |
| L93-2086 | CAMR |
| LE187 | CAMR |
| 310555 | CAMR |
| L93-2411 | CAMR |
| L93-2539 | CAMR |
| L90-1252 | CAMR |
| 2043 | CAMR |
| 8310626 | CAMR |
| E91049 | Dr C Ison, ICSM |
| E85025 | Dr C Ison, ICSM |
| E57814 | Dr C Ison, ICSM |
| H73869 | Dr C Ison, ICSM |
| H98632 | Dr C Ison, ICSM |
| H9866 | Dr C Ison, ICSM |
| H99424 | Dr C Ison, ICSM |
| H98914 | Dr C Ison, ICSM |
| Copenhagen | Dr C Ison, ICSM |
| ATCC-23970 | Dr. S Gray, Manchester PHL |
| M99-243079 | Dr. S Gray, Manchester PHL |
| M99-243086 | Dr. S Gray, Manchester PHL |
| M99-243325 | Dr. S Gray, Manchester PHL |
| M99-243350 | Dr. S Gray, Manchester PHL |
| M99-243361 | Dr. S Gray, Manchester PHL |
| 2018 | Dr I Feavers, NIBSC |
| 039-03 L582 | Dr M Maiden, University of Oxford |
| 066-10 L583 | Dr M Maiden, University of Oxford |
| 028-12 L584 | Dr M Maiden, University of Oxford |
| 030-24 L585 | Dr M Maiden, University of Oxford |
| 014-24 L586 | Dr M Maiden, University of Oxford |
| 094-24 L590 | Dr M Maiden, University of Oxford |
| 049-12 L591 | Dr M Maiden, University of Oxford |
| 058-24 L593 | Dr M Maiden, University of Oxford |
| 016-24 L594 | Dr M Maiden, University of Oxford |
| 004-12 L595 | Dr M Maiden, University of Oxford |
| 057-08 L596 | Dr M Maiden, University of Oxford |
| 088-05 L597 | Dr M Maiden, University of Oxford |
| 085-12 L600 | Dr M Maiden, University of Oxford |
| 09002s1 L601 | Dr M Maiden, University of Oxford |
| 090-10 L603 | Dr M Maiden, University of Oxford |
| 8206 L604 | Dr M Maiden, University of Oxford |
| 005-24 L607 | Dr M Maiden, University of Oxford |
| 017-02 L608 | Dr M Maiden, University of Oxford |
| 10102m L613 | Dr M Maiden, University of Oxford |
| 4116 L615 | Dr M Maiden, University of Oxford |
| 224 L624 | Dr M Maiden, University of Oxford |

-continued

| N. lactamica strains | Source |
|---|---|
| 4408 L628 | Dr M Maiden, University of Oxford |
| 012-12 L631 | Dr M Maiden, University of Oxford |
| 081-24 L633 | Dr M Maiden, University of Oxford |
| 020-06 L640 | Dr M Maiden, University of Oxford |
| 005-12 L642 | Dr M Maiden, University of Oxford |
| 310 L643 | Dr M Maiden, University of Oxford |
| 620 L644 | Dr M Maiden, University of Oxford |

| N. cinerea strains | Source |
|---|---|
| Copenhagen | Dr C Ison, ICSM |
| NRL 32165 | Dr J Knapp, CDC Atlanta |
| 2829 | Dr I Feavers, NIBSC |
| 369 | Dr C Ison, ICSM |

| N. flavescens strains | Source |
|---|---|
| 2017 | Dr I Feavers, NIBSC |
| 2830 | Dr I Feavers, NIBSC |
| 2831 | Dr I Feavers, NIBSC |
| 2832 | Dr I Feavers, NIBSC |

| | Source |
|---|---|
| N.sicca strains | |
| M97-252234 | Dr. S Gray, Manchester PHL |
| M97-252086 | Dr. S Gray, Manchester PHL |
| M97-251336 | Dr. S Gray, Manchester PHL |
| M97-252638 | Dr. S Gray, Manchester PHL |
| Miscellaneous commensal Neisseria strains | |
| N. mucosa 2833 | Dr I Feavers, NIBSC |
| N. polysaccharea 2834 | Dr I Feavers, NIBSC |
| N. polysaccharea 370 | Dr C Ison, ICSM |
| N. flava NRL 30008 | Dr J Knapp, CDC Atlanta |
| N. subflava NRL 30017 | Dr J Knapp, CDC Atlanta |
| N. sp M98 251221 | CAMR |
| N. sp M98 251544 | CAMR |
| N. sp M97 252638 | CAMR |

2.1.2 Bacterial Growth Conditions

*Escherichia coli* strains were used as the host strains for cloning experiments. E. coli strains were grown on Luria-Bertani (LB) plates (Oxoid, Unipath, UK) at 37° C. in 5% $CO_2$ or in LB broth at 37° C. in an orbital incubator at 200 rpm (Sambrook, 1989).

Neisserial strains were cultured on GC (gonococcal) agar (Difco, UK) supplemented with 1% Vitox (sGC) (Oxoid) at 37° C. in 5% $CO_2$. Broth culture of Neisserial strains was undertaken in Mueller-Hinton (MH) broth (Oxoid, UK) supplemented with 1% Vitox (sMH) at 37° C. in an orbital incubator at 180 rpm.

2.2 Identification and Typing of Neisserial Strains 2.2.1 Gram Stain

Bacteria were harvested from overnight plates and resuspended in phosphate buffered saline (PBS),(0.01 M phosphate buffer, 0.0027M potassium chloride and 0.137M sodium chloride, pH 7.4). This suspension was transferred to a microscope slide and air-dried. The bacteria were heat-fixed to the slide by passing through a flame. The slide was flooded in turn with crystal violet (Pro-lab Diagnostics) for 1 min, Gram's iodine (Pro-lab Diagnostics) for 1 min, acetone for 5 sec, neutral red (Pro-lab Diagnostics) for 1 minute before washing with water and allowed to air-dry. Slides were examined using a light microscope (Olympus BH2).

2.2.2 API Strips

The API NH system, based on 12 identification tests, was used to identify various neisserial sp. The tests were carried out according to the manufacturers instructions (BioMerieux, France).

2.3 Generation of Nalidixic Acid Resistant Commensal Neisserial Strains

Wild-type Neisserial strains were cultured overnight on sGC agar plates. Bacteria from the overnight plates were harvested into 10 ml of sMH broth to a starting OD600 of approximately 0.2, and cultured in a shaking incubator for 8 to 10 hours. 10 ml of sMH broth containing nalidixic acid to a final concentration of 10 μg/ml was added to the culture, which was then incubated overnight. The overnight culture was centrifuged at 4° C. for 10 minutes at 2500 rpm, and the pellet resuspended in 100 to 200 μl of residual media. Bacteria were plated onto sGC agar plates containing 20 μg/ml nalidixic acid. Single colonies were sub-cultured and evaluated by colony morphology and Gram stain.

2.4 Conjugation of Commensal *Neisseria* Strains

*E. coli* S17-1 l pir donor strains, containing plasmid, were grown overnight in LB broth containing 75 μg/ml kanamycin, then diluted 1:100 in sMH broth with no antibiotics, and incubated without shaking for 1.5 hours at 37° C. in 5% $CO_2$. Overnight plates of the recipient nalidixic acid resistant *Neisseria* strains were harvested into 5 ml of pre-warmed sMH broth (approximately $10^8$ CFU/ml) and diluted 1:50 in 50 ml of pre-warmed sMH broth. This subculture was incubated without shaking for 2 to 4 hours at 37° C. with 5% $CO_2$ in a 50 ml flask which allows a high surface to volume ratio. 300 μl recipient and 50 μl donor cells from these subcultures were pipetted onto a 0.45 μM pore size membrane filter (MILLIPORE®) placed on a sGC agar plate, which were then incubated overnight. The filters were scraped and/or vortexed into 5 ml of MH broth in a 50 ml skirted tube. The filter was removed and the suspension was centrifuged at 3000 g for 10 min. The pellet was resuspended in 100 to 200 μl of residual media before being plated onto GC plates containing 20 μg/ml nalidixic acid and 75 μg/ml kanamycin. These plates were incubated overnight and single colonies selected for further evaluation.

2.5 Transformation of *E. coli* Strains

Aliquots of TOP10 and S17-1 λpir competent cells were thawed on ice, following removal from storage at −70° C. Transforming DNA was added to 50 μl of competent cells, and incubated on ice for 30 minutes. This mixture was exposed to heat-shock of 42° C. for 90 seconds and returned to ice for 5 minutes. The mixture was added to 1 ml of supplemented SOC media and incubated for 1 hour at 37° C. in an orbital incubator at 200 rpm. This culture was pelleted by centrifugation at 8,000 rpm for 3 min, and then plated onto selective agar plates. Plates were incubated overnight, and single colonies were picked and evaluated by plasmid extraction and digest and/or PCR.

2.6 Preparation of Outer Membrane Vesicles (OMVs)

Commensal *Neisseria* strains were grown to stationary phase in Frantz medium (8.7 mM L-glutamic acid, 0.076 mM L-cysteine HCL, 0.016 M $NaH_2PO_4.2H_2O$, 0.001 M KCl, 0.1 M NaCl, 0.02 M $NH_4Cl$, 0.002 M $MgSO_4.7H_2O$, 0.5% glucose, 0.2% yeast extract, pH 7.3) and extracted with the detergent deoxycholate. Outer membrane vesicles (OMV) were purified by ultracentrifugation as described in (Fredriksen etal., 1991).

2.7 DNA Extraction 2.7.1 Purification of Plasmid DNA from *E. coli*

Plasmid DNA was purified from *E. coli* host cells using QIA Spin® plasmid kit or QIAGEN® plasmid midi kit according to the manufacturers instructions (Qiagen, UK). The protocols were based on a modified alkaline lysis procedure followed by binding plasmid DNA to a QIAGEN® anion-exchange resin under appropriate low salt and pH conditions.

2.7.2 Purification of Plasmid DNA from *Neisseria* sp.

*Neisseria* strains were grown to confluence on sGC agar plates with appropriate antibiotics when necessary. The bacteria were harvested from three plates and plasmid DNA was purified using the QIAGEN® plasmid midi kit according to the manufacturers instructions (Qiagen, UK).

2.7.3 Chromosomal DNA Extraction

*Neisseria* strains were grown to confluence on GC agar plates with appropriate antibiotics when necessary. The bacteria were harvested from a single plate and chromosomal DNA isolated using the QIAGEN® Genomic-tip System according to the manufacturers instructions (Qiagen, UK).

2.7.4 Purification of DNA from Agarose Gels

DNA fragments were excised from agarose gels, to which ethidium bromide was added, using a scalpel blade whilst DNA was visualised using a UV transilluminator (302 nm). DNA was purified from the agarose gel using a QIAquick® gel extraction kit according to the manufacturers instructions (Qiagen, UK).

2.8 Enzyme Modification of Plasmid DNA 2.8.1 Restriction Endonucleases

Restriction enzymes were used according to manufacturers instructions (Roche, UK). The reaction products were analysed by agarose gel electrophoresis using TAE (0.04M Tris acetate, 0.001M EDTA, pH 8.0) as a buffer.

2.8.2 DNA Ligation

Ligation reactions were performed in 0.5 ml centrifuge tubes containing T4 ligase, ligase buffer with a final concentration of 50 mM Tris HCl pH 7.8, 10 mM Mg $Cl_2$, 10 mM DTT (dithiothreitol), 10 mM ATP, 25 μg/ml bovine serum albumin and distilled $H_2O$ to 10 ml if required. Typically the molar concentration of insert was 3 times the concentration of vector. The reaction was incubated overnight at 16 ° C.

2.9 Polymerase Chain Reaction (PCR)

2.9.1 PCR

PCR reactions consisted of DNA, 1 pmol/μl of each primer (Table 2.1), 0.2 mM dNTPs (deoxyribonucleoside triphosphates), 0.5 units HotStar® Taq DNA polymerase (Qiagen, UK), and PCR buffer with a final concentration of 100 mM Tris-HCl, 500 mM KCl, 15 mM $MgCl_2$ Reactions were performed in a programmable heating block (Perkin Elmer).

PCR amplification of DNA was carried out as follows. The first cycle consisted of 15 min activation of Taq at 95° C., 1 min of denaturation at 94° C., annealing at 45° C. for 1 min and polymerisation at 72° C. for 2 min. The subsequent 30 cycles contained denaturation for 1 min at 94° C., annealing for 1 min at 45° C. and polymerisation at 72° C. for 2 min. The final cycle consisted of polymerisation at 72° C. for 10 min.

TABLE 2.1

Primers used in PCR reactions.

| Primer | Sequence 5' to 3' | Target sequence | SEQ ID NO: |
|---|---|---|---|
| 401US | GCAGTCTCTCGAGCTCAAG | pMIDG100 | 1 |
| 411DS | CCTCTCCACTGACAGAAAA | pMIDG100 | 2 |
| M13F | GTAAAACGACGGCCAGT | pUC19/pZero-2 | 3 |
| M13R | AACAGCTATGGACCATG | pUC19/pZero-2 | 4 |

2.9.2 Colony PCR

Colony PCR using HYBAID® recovery amplification reagent (Hybaid Ltd, UK) was carried out according to the manufacturers instructions. The Hybaid reagent works by sequestering cell lysis products, which may inhibit polymerases and improves amplification yield and specificity.

2.9.3 Sequencing

Automated PCR cycle sequencing was carried out according to the manufacturers instructions (Applied Biosystems International, USA). Taq Dye-deoxy cycle sequencing was performed on samples containing 4.0 ml terminator ready action mix; 500 ng/ml double stranded DNA template, 1.6 pmol primer and $H_2O$ to a final volume of 10 ml.

Table 2.2: Primers Used in Sequencing Reactions

TABLE 2.2

Primers used in sequencing reactions.

| Primer | Sequence 5' to 3' | Target sequence | SEQ ID NO: |
|---|---|---|---|
| 401US | GCAGTCTCTCGAGCTCAAG | pMIDG200 backbone | 5 |
| MIDG200 DS | CGCTTTACACTTTATGCTTCCG | pMIDG200 backbone | 6 |
| M13F | GTAAAACGACGGCCAGT | pUC19/pZero-2 | 7 |
| M13R | AACAGCTATGGACCATG | pUC19/pZero-2 | 8 |

2.10 Southern Hybridisation 2.10.1 Gel

The DNA was digested with an appropriate enzyme, typically ClaI, loaded onto a 0.8% agarose gel and the fragments separated by electrophoresis. The gel was washed for 10 min in depurinating solution (0.25M HCl); then washed twice for 15 min in denaturing solution (1.5M NaCl, 0.5M NaOH) and neutralising solution (0.5M Tris pH 7.2–7.5, 1.5M NaCl, 1 mM EDTA) in turn. The gel was placed on a clean glass plate. A piece of nylon membrane cut to fit the gel was layered onto the gel taking care to eliminate all air bubbles trapped between the gel and the membrane. Three pieces of 3MM filter paper were soaked in neutralization solution before being placed on top of the membrane. 30–50 mm of dry paper towels were placed on top the wet filter paper; followed by another glass plate and one or two litre bottle filled with water to compress the sandwich. 60–90 min was allowed for transfer. The DNA was fixed to the membrane using an ultraviolet cross-linker.

2.10.2 Probe Labelling

DIG (Roche, UK) labelled DNA probes were generated according to the method of random primed labelling which is based on the hybridisation of random oligonucleotides to the denatured template. The complementary DNA strand was synthesized by Klenow enzyme, which used the 3' OH termini of the random oligonucleotides as primers and a mixture of deoxyribonucleotides containing DIG-11-dUTP alkali-labile for elongation, resulting in the incorporation of digoxigenin into the newly synthesized DNA.

2.10.3 Hybridisation and Detection

Southern hybridisation was carried out according to manufacturers instructions, (Roche, UK). The hybridised blot under went chemiluminescent detection, a three-step process. The membranes were first treated with blocking reagent to prevent non-specific attraction of antibody to the membrane, followed by incubation with a dilution of anti-digoxigenin Fab fragments, which were conjugated to alkaline phosphatase. Finally the membrane carrying the hybridised probe and bound antibody conjugate was reacted with a chemiluminescent substrate and exposed to X-ray film to record the chemiluminescent signal.

2.11 SDS-PAGE

SDS-PAGE was performed as described in (Sambrook, 1989) using Protogel (BioRad®) 30% acrylamide/bis solution, 37.5:1 (2.6% C) and BioRad® Protean II kit. The gels were run at 25 mA per gel.

2.12. Staining 2.12.1 Coomassie Stain

Coomassie staining was performed as described in (Sambrook, 1989). The gels were stored in 55% methanol and 0.2% glycerol until drying.

2.12.2 Amido Black Stain

Amido black staining was performed as described in (Gershoni et al., 1982).

Briefly nitrocellulose membranes were stained in 0.1% amido black, 25% isopropanol and 10% acetic acid, and destained in 25% isopropanol and 10% acetic acid.

2.13 Western Hybridisation 2.13.1 Transfer and Hybridisation

Transfer of protein to nitrocellulose was performed as described by (Sambrook, 1989). The Western hybridisation procedure was a three-step process leading to antigens immobilised on membranes being detected with antibodies. First the primary rabbit antiserum, directed against a specific antigen was added to bind potential antigenic sites. In the second step, the secondary antibody, an anti rabbit IgG enzyme conjugate, was added to bind to the primary antibody. The enzyme (alkaline phosphatase or horse radish peroxidase) conjugated to the secondary antibody catalysed a light reaction in the third step, when the appropriate substrate was added.

2.13.2 Detection

Detection using ECL:

The ECL plus detection system allows light to be produced by the oxidation of luminol in the presence of an enhancer, with horseradish peroxidase acting as a catalyst. The resulting light was captured on X ray film.

Detection using 4-chloro-naphthol solutions:

The blotted nitrocellulose was developed by incubation in 4-chloro-naphthol solution prepared as per manufacturer's instruction (Sigma UK). The blot was washed in PBS before scanning using multi-analyst software.

2.14 Detection of GFP Expression by Fluorescence Activated Cell Sorting (FACS)

2.14.1 Preparation of Cells

Neisseria cells were fixed in 1:1 Facsfix, a solution of 2% formaldehyde and 2% glucose in phosphate buffered saline (PBS). When stained with propidium iodide samples were mixed with 1:1000 of 1 mg/ml of propidium iodide. Fixed cells were stored at 4° C. and evaluated by flow cytometry within 3 days.

2.14.2 Ultraviolet Microscopy

Ultraviolet microscopy was performed using filters suitable for the examination of fluorescein isothiocyanate fluorophores, which results in peak excitation at 490 nm (Olympus BH2).

2.14.3 FACS

The fluorescent signal from Neisserial strains expressing GFP was quantified using a FACS Calibur flow cytometer (Becton-Dickinson) running CELLQUEST® software (Becton-Dickinson). The flow cytometer settings used were as follows: FSC (channel EO2, log scale), SSC (log scale, amplification=566, threshold=398), FL1-H (log scale, amplification=674), and FL3-H (log scale, amplification=705). Low flow rates were used for the evaluation of all samples.

3: Expression of Antigens 3.1 Introduction

The commensal Neisseria were studied for their capacity to take up pMIDG100 and allow GFP expression. pMIDG100 is a reporter plasmid, which replicates in both E. coli and N. meningitidis. It contains aphA-3 encoding an aminoglycoside modifying enzyme that inactivates kanamycin, a rho-independent upstream transcriptional terminator, a multiple cloning site, a ribosome binding site (RBS), a promotorless green fluorescent protein (gfp) gene (gfpmut3) and a downstream transcriptional terminator. pMIDG100 has the potential to be modified to allow the expression of foreign antigens that confer desirable vaccine properties by removing the gene gfp encoding the present antigen, and adapting the vector to include a multiple cloning site (to aid cloning of antigens) and a promoter to drive expression.

3.2 Screening of Commensal Neisseria 3.2.1 Generation of Nalidixic Acid Resistant Recipient Strains A collection of commensal Neisseria strains was assembled with the generous help of Dr. C. Ison at ICSM, Dr. I. Feavers at NIBSC, Dr J. Knapp at the Centre for Disease Control, Atlanta, Dr. S. Gray at the Meningococcal Reference Unit in Manchester Public Health Laboratory, and Dr M. Maiden at the University of Oxford. All strains were screened for natural resistance to nalidixic acid and kanamycin, the markers to be used in the conjugation protocol. None were naturally nalidixic acid or kanamycin resistant at levels of 20 µg/ml and 75 µg/ml respectively. Nalidixic acid resistance was induced in all the commensal Neisseria strains by exposure of strains grown to stationary phase in broth culture to a low concentration of nalidixic acid, followed by overnight growth on selection media to select for spontaneous gyrase mutants.

3.2.2 Conjugation of pMIDG100 and pMIDG101 into Various Commensal Neisseria

A literature review revealed a paper describing conjugation-positive strains of commensal Neisseria (Genco et al., 1984). Three of these conjugation-positive strains, N. cinerea NRL32165, N. flava NRL30008 and N. subflava NRL30017, were kindly provided by Dr J Knapp at CDC, Atlanta. pMIDG100 (carrying the promoterless gfp gene) and pMIDG101 (pMIDG100 which contains the strong constitutive ner promoter) have now been successfully conjugated into the above strains and a further three N. cinerea strains (N. cinerea Copenhagen, N. cinerea 2829, N. cinerea 369), two N. flavescens strains (N. flavescens 2830, N. flavescens 2017) and two N. sicca strains (N. sicca M97-251336, N. sicca M98-252234). Colonies were initially screened by colony PCR with primers designed against the pMIDG100 backbone in order to check for the presence of the plasmids. An identical result was seen for both conjugation positive N. sicca strains harbouring the plasmid, result not shown.

Two clones for each conjugation positive strain were selected, one containing pMIDG100 the other pMIDG101, and a QAIGEN® midi-prep was carried out to re-isolate the plasmid to ensure the plasmid had not inserted into the chromosomal DNA. Restriction digests verified the presence of intact pMIDG100 and pMIDG101.

3.3 Detection of GFP Expression 3.3.1 Expression Detected by FACS

FACS analysis was carried out using the five commensal strains (N. cinerea NRL32165, N. sicca M98-252234, N. flavescens 2830, N. flava NRL30008, N. subflava NRL30017) previously shown to take up intact pMIDG100 and pMIDG101. Strains were harvested from overnight plates, washed in PBS and killed by the addition of 2% formaldehyde. The commensal strains expressing pMIDG101 were evaluated using FACS analysis and compared with cells containing pMIDG100. FL1-H histograms comparing these cells are displayed in FIG. 8, and show through a rightward shift in fluorescence, that cells expressing GFP under the control of the strong ner promoter (pMIDG 101) have a substantially greater fluorescence than those expressing promoterless gfp (pMIDG100). The mean fluorescence for each strain is detailed in table 3.1.

Table 3.1 Summary of FACS Analysis

The mean fluorescence for each commensal strain harbouring either pMIDG100 or pMIDG101 is shown in the table below. Cells expressing GFP under the control of the ner promoter (pMIDG101) have a greater fluorescence than those expressing promoterless gfp (pMIDG100).

| Strain | Mean fluorescence pMIDG100 | Mean fluorescence pMIDG101 |
|---|---|---|
| N. cinerea NRL32165 | 17.16 | 121.5 |
| N. flavescens 2830 | 12.51 | 155.38 |
| N. sicca M98-252234 | 9.90 | 47.44 |

-continued

| Strain | Mean fluorescence pMIDG100 | Mean fluorescence pMIDG101 |
|---|---|---|
| N. flava NRL30008 | 13.79 | 142.37 |
| N. subflava NRL30017 | 9.80 | 62.23 |

3.3.2 Western Blotting

GFP expression was also detected from whole cells by Western blot analysis.

Commensal Neisseria strains N. cinerea NRL32165, N. sicca M98-252234, N. flavescens 2830, N. flava NRL30008, N. subflava NRL30017, wild-type and containing pMIDG100 and pMIDG101, were grown overnight on sGC agar plates. Bacteria were harvested into 2 ml PBS, washed and the pellet resuspended in reducing buffer (0.125M Tris pH6.8, 4% SDS, 50% glycerol, 10% β-Mercaptoethanol). The samples were separated on a 12% SDS PAGE gel, blotted and GFP detected using anti-GFP antibody conjugated to horseradish peroxidase.

Western Blot Analysis—see FIG. 9

GFP expression in the commensal Neisseria was detected using anti-GFP antibody conjugated to horseradish peroxidase. GFP is detected in the strains harbouring the pMIDG101 plasmid.

Figure 9A:
FIGS. 9A and 9B show detection of GFP expression by western blot in commensal *Neisseria* using anti-GFP antibody conjugated to horseradish peroxidase, GFP being detected in strains harbouring the pMIDG101 plasmid.

In FIG. 9A: Lane 1, GFP; 2, N. cinerea NRL32165 wild-type; 3, N. cinerea NRL32165 pMIDG100; 4, N. cinerea NRL32165 pMIDG101; 5, N. subflava NRL30017 wild-type; 6, N. subflava NRL30017 pMIDG 100; 7, N. subflava NRL30017 pMIDG101; 8, N. flava NRL30008 wild-type; 9, N. flava NRL30008 pMIDG100; 10, N. flava NRL30008 pMIDG101

Figure 9B:
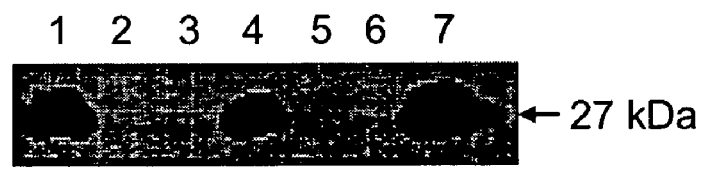

In FIG. 9B: Lane 1, GFP; 2, N. flavescens 2830 wild-type; 3, N. flavescens 2830 pMIDG100, 4, N. flavescens 2830 pMIDG101; 5, N. sicca M98-252234 wild-type; 6, N. sicca M98-252234 pMIDG100; 7, N. sicca M98-252234 pMIDG101

There was no expression of GFP from the commensal Neisseria (N. cinerea, N. sicca, N. flavescens, N. flava, N. subflava) wild-type strains or those harbouring pMIDG100 (promoterless gfp) in contrast to strains harbouring pMIDG101 (gfp under control of the ner promoter). The Western blotting clearly demonstrates that whole cells from the commensal Neisseria strains express the GFP under the control of the ner promoter.

3.4 Construction of the pMIDG200 Series of Plasmids

To allow the expression of foreign antigens the pMIDG 100 series of vectors containing various promoters has been modified to remove the gfp gene, which was replaced with a multiple cloning site. The rationale behind the use of a variety of promoters was that optimal expression of different foreign antigens might require different levels of promoter activity or in cases where antigen expression could adversely affect bacterial growth it may best be achieved with a tightly regulated promoter. The pMIDG100 series of plasmids contains a bank of promoters, which have been evaluated in serogroup B N. meningitidis under a variety of environmental conditions. Four promoters from this bank were selected—two constitutive and two regulated (see table 3.2). The regulated promoters, inducible in meningococcus under defined environmental conditions, were those relating to the gene for a heat shock protein groES/EL (Pannekoek et al., 1995), and to frpC, encoding an iron-regulated protein, a member of the RTX-cytolysin family (Thompson et al., 1993a; Thompson et al., 1993b). The constitutive promoters, which were known to drive GFP expression in different environments including different growth phases, whole blood, iron-restriction and acidic conditions, were those relating to recA, encoding a protease which is part of the SOS DNA repair system and to the ner operon. In serogroup A meningococcus this is thought to be regulated by negative feedback, via the ner repressor (Goosen et al., 1984; Kukoij et al., 1992; Tolias et al., 1985). In serogroup B strains the ner promoter is strongly on.

Table 3.2 Summary of Promoters

Baseline GFP expression was evaluated by growing meningococci overnight of sGC plates and analysing by FACS analysis. The mean baseline fluorescence for each plasmid is detailed in the table below.

| Construction | promoter | Mean fluorescence (x pMIDG100) |
|---|---|---|
| pMIDG100 | promoterless | 1.0 |
| pMIDG101 | ner | 32.2 |
| pMIDG102 | frpC | 1.51 |
| pMIDG103 | recA | 1.59 |
| pMIDG104 | groES/EL | 2.57 |

DNA was isolated from pMIDG101, pMIDG102, pMIDG103 and pMIDG104 and digested with BamHI and XbaI to remove the gfp gene and transcriptional terminator however leaving the cloned promoters, which are present, intact. The fragment containing the pMIDG100 backbone and promoter was purified by agarose gel electrophoresis using a QIAGEN® gel extraction kit. Single stranded DNA oligonucleotides corresponding to the two strands of the sequence shown below were synthesised.

Sequence of Linker (SEQ ID NOS: 9 and 10)

The linker was design to contain several unique restriction sites and the neisserial uptake sequence, which may aid transformation. Restriction sites are boxed:

```
5'BamHI  NotI     SnaBI  NcoI         SmaI        PstI
  GATCCCGGCGGCCGCTACGTACCATGGGAGCTGCCCGGGGTCCAGCTGCAG
     GGGCCGCCGGCGATGCATGGTACCCTCGACGGGCCCCAGGTCGACGTC

GCCGTCTGAATCATTTCAGACGGCT
CGGCAGACTTAGTAAAGTCTGCCGAGATC
Neisserial uptake seq.   XbaI 3'
```

These oligonucleotides (SEQ ID NOS: 9 and 10) were annealed by boiling at 100° C. for 5 min in ligase buffer and cooling to 4° C. Initial attempts at cloning the linker directly into the pMIDG100 backbone were unsuccessful. The linker was ligated to pUC19 digested with BamHI and XbaI and the ligation mix transformed into chemically competent E. coli TOP 10 cells. Two clones were selected. Plasmid was purified and sequenced using vector specific primer M13F. One clone was found to have the expected linker sequence confirming that the BamHI and XbaI sites were intact. The linker was cut out of pUC19, separated from the vector, and ligated to the backbone of the pMIDG100 series of vectors. The ligation mix was transformed into chemically competent E. coli TOP 10 cells. Twelve transformants of each construct were screened by colony blots, probing with DIG labelled linker: approximately 10 clones were shown to hybridise to the linker. Two clones containing each plasmid construct were QIAGEN® purified, analysed by restriction digest and one clone was selected for sequencing. This confirmed that the sequenced clones were the desired construct and these were called pMIDG201 (ner promoter), pMIDG202 (frpC promoter), pMIDG203 (recA promoter), and pMIDG204 (groES/EL promoter) respectively.

3.5 Summary

The FACS and Western results clearly demonstrate that the commensal Neisseria sp. harbouring pMIDG101 express GFP under the control of the ner promoter.

4: Preparation of OMVs and Cross Reacting Antigens in Neisserial sp.

4.1 Introduction

Meningococci release large amounts of outer membrane vesicles (OMVs) into broth culture during growth. These OMVs or blebs contain OMPs and LOS; suitably detoxified preparations may be used as vaccines (Fredriksen et al., 1991).

4.2 OMVs

OMVs were prepared from a selection of commensal Neisseria strains, N. cinerea NRL32165, N. cinerea Copenhagen, N. flavescens 2830, N. flava NRL30008, N. subflava NRL30017.

The proteins from the OMV preparations were separated on a 10% SDS PAGE gel, blotted and probed with rabbit sera raised against OMVs from N. meningitidis MC58, N. meningitidis MC58 capsule minus, N. meningitidis K454, N. lactamica Y921009 and N. cinerea NRL32165. These results clearly indicate that cross-reacting antigens are present between various Neisseria sp.

OMVs have thus been prepared from several commensal Neisseria strains (N. cinerea, N. lactamica, N. flava, N. subflava and N. flavescens) indicating that release of OMVs during growth is not limited to the pathogenic Neisseria sp., N. meningitidis and N. gonorrhoeae.

EXAMPLE 12

1 Expression of Meningococcal Antigens in Commensal Neisseria 1.1 Introduction

In this example, following the techniques set out in Example 11, we have expressed the meningococcal antigen NspA in commensal Neisseria, allowing for example the natural protection offered by these non-pathogenic bacteria against meningococcal disease to be enhanced.

In previous examples, it has been clearly established with the gfp constructions, that foreign genes can be expressed from plasmid conjugated into commensal Neisseria. Vectors to enable this work to be extended to the expression of a potential meningococcal vaccine antigen have been constructed for expression of meningococcal antigen, with the first antigen that will be expressed being Neisserial surface protein A (NspA) a highly conserved OMP, which has been shown to be present in all of 250 N. meningitidis strains (Martin et al., 1997).

Based on the GenBank nucleotide sequence of N. meningitidis nspA two cassettes have been designed. Cassette I contains a copy of nspA, with its "native" upstream sequence, RBS and rho-independent terminator. Cassette II has an alternative 5' end (NcoI site—TTTTTG GAGAATTGACCATG) (SEQ ID NO: 11) that places a different RBS, known to work well in the pMIDG100 vector, with its surrounding bases in front of nspA. The nspA "cassettes" have been be cloned into the pMIDG200 series of vectors and expressed.

1.2 Expression Studies

To screen for expression of NspA in commensal Neisseria, a dot blot was carried out using Me-7 NspA monoclonal antibody (as described in the publication of Cadieux et al. (1999 September) Infect. Immun. 67(9): 4955–9 on the following, using the A and B cassettes and promoters as set out:

1 N. cinerea wild-type
2 N. sicca wild-type
3 N. flavescens wild-type
4 N. subflava wild-type
5 N. flava wild-type
6 E. coli Top10 pMIDG202 (FrpC) with NspA cassette A
7 E. coli Top10 pMIDG202 (FrpC) with NspA cassette B
8 E. coli Top10 pMIDG204 (gro) with NspA cassette A
9 E. coli Top10 pMIDG204 (gro) with NspA cassette B
10 E. coli Top10 pMIDG201 (ner) with NspA cassette B
11 E. coli Top10 pMIDG203 (RecA) with NspA cassette A
12 E. coli Top10 pMIDG203 (RecA) with NspA cassette B This showed no expression of NspA in N. cinerea, N. sicca, N. flavescens, N. subflava or N. flava, confirming there is no native expression of NspA, but expression in E. coli using the pMIDG vector. We then attempted to express NspA in commensal Neisseria using the A and B cassettes and the promoters as set out below:—

1 wild-type
2 pMIDG202 (FrpC) with NspA cassette A
3 pMIDG202 (FrpC) with NspA cassette B
4 pMIDG204 (gro) with NspA cassette A
5 pMIDG204 (gro) with NspA cassette B
6 pMIDG203 (RecA) with NspA cassette A
7 pMIDG203 (RecA) with NspA cassette B
8 pMIDG201 (ner) with NspA cassette B This set of plasmids was conjugated into each of N. flavescens 2830, N. subflava NRL 30017, N. cinerea NRL 32165, N. flava NRL 30008, N. sicca M97-252234.

Clear expression of NspA was seen in N. flavescens, N. subflava, and N. cinerea. The background binding of the NspA Mab was high with N. sicca and N. flava, though expression was also seen in these two latter commensals.

EXAMPLE 13

Outer membrane vesicles (OMVs) were prepared from N. lactamica strain Y92-1009, N. meningitidis strain K454 and N. cinerea strain NRL321 65 using the method described in Example 2. Mice were vaccinated and challenged with N. meningitidis as described in Example 4. It can be seen (FIG. 12) that the N. lactamica OMV provide equivalent or better protection than the meningococcal OMV against challenge with meningococcal strains representing the ET5, ET37, lineage 3 and cluster A4 clonal lineages. It can also be seen that *N. cinerea* OMVs provide protection against challenge with meningococcal strain K454.

EXAMPLE 14

Outer membrane vesicles were prepared from *N. lactamica* strain Y92-1009 as described in Example 2. The low molecular weight subfraction was prepared as described in Example 5. Mice were vaccinated and challenged with *N. meningitidis* as described in Example 4. This illustrates protection provided by the *N. lactamica* OMVs and low molecular weight subfraction against challenge with two serogroup B meningococcal strains and 2 serogroup C strains (FIG. 13).

EXAMPLE 15

This example demonstrates that the *N. lactamica* OMVs and low molecular weight subfractions provide mice with protection against meningococcal challenge when the vaccines are administered with Freund's adjuvant and pharmaceutically acceptable alum adjuvant (see FIG. 14). Methods are as above.

The invention thus provides immunogenic compositions and vaccines for use in protecting against disease.

References:

Bjune, G., Hoiby, E. A., Gronnesby, J. K., Arnesen, O., Fredriksen, J. H., Halstensen, A., Holten, E., Lindbak, A. K., Nokleby, H., Rosenqvist, E. and et al. (1991) Effect of outer membrane vesicle vaccine against group B meningococcal disease in Norway [see comments]. *Lancet*, 338, 1093–6.

Fredriksen, J. H., Rosenqvist, E., Wedege, E., Bryn, K., Bjune, G., Froholm, L. O., Lindbak, A. K., Mogster, B., Namork, E., Rye, U. and et al. (1991) Production, characterization and control of MenB-vaccine "Folkehelsa": an outer membrane vesicle vaccine against group B meningococcal disease. *NIPH Ann*, 14, 67–79; discussion 79–80.

Genco, C. A., Knapp, J. S. and Clark, V. L. (1 984) Conjugation of plasmids of *Neisseria gonorrhoeae* to other *Neisseria* species: potential reservoirs for the beta-lactamase plasmid. *J Infect Dis*, 150, 397–401.

Gershoni, J. M. and Palade, G. E. (1 982) Electrophoretic transfer of proteins from sodium dodecyl sulfate-polyacrylamide gels to a positively charged membrane filter. *Anal Biochem*, 124, 396–405.

Goosen, N. and van de Putte, P. (1984) Regulation of Mu transposition. I. Localization of the presumed recognition sites for HimD and Ner functions controlling bacteriophage Mu transcription. *Gene*, 30, 41–6.

Hanahan, D. (1 983) Studies on transformation of *Escherichia coli* with plasmids. *J Mol Biol*, 166, 557–80.

Ison, C. A., Anwar, N., Cole, M. J., Galassini, R., Heyderman, R. S., Klein, N. J., West, J., Pollard, A. J., Morley, S., Levin and the Meningococcal, R. (1 999) Assessment of immune response to meningococcal disease: comparison of a whole-blood assay and the serum bactericidal assay. *Microb Pathog*, 27, 207–14.

Knapp, J. S., and Hook, E. W. d. (1988) Prevalence and persistence of *Neisseria cinerea* and other *Neisseria* spp. in adults. *J Clin Microbiol*, 26, 896–900.

Kukoij, G., and DuBow, M. S. (1992) Integration host factor activates the Ner-repressed early promoter of transposable Mu-like phage D108. *J Biol Chem*, 267, 17827–35.

Martin, D., Cadieux, N., Hamel, J. and Brodeur, B. R. (1997) Highly conserved *Neisseria meningitidis* surface protein confers protection against experimental infection. *J Exp Med*, 185, 1173–83.

Pannekoek, Y., Dankert, J. and van Putten, J. P. (1995) Construction of recombinant neisserial Hsp6O proteins and mapping of antigenic domains. *Mol Microbiol*, 15, 277–85.

Sambrook, F., Maniatis. (1989) *Molecular Cloning. A laboratory Manual*. Cold Spring Harbor Laboratory Press.

Simon, R., Priefer U and Puhler A. (1983) A broad host range mobilization system for in vivo genetic engineering Gram negative bacteria. *Bio/Technology*, 1, 784–791.

Thompson, S. A., Wang, L. L. and Sparling, P. F. (1993a) Cloning and nucleotide sequence of frpC, a second gene from *Neisseria meningitidis* encoding a protein similar to RTX cytotoxins. *Mol Microbiol*, 9, 85–96.

Thompson, S. A., Wang, L. L., West, A. and Sparling, P. F. (1993b) *Neisseria meningitidis* produces iron-regulated proteins related to the RTX family of exoproteins. *J Bacteriol*, 175, 811–8.

Tolias, P. P., and DuBow, M. S. (1985) The cloning and characterization of the bacteriophage D108 regulatory DNA-binding protein ner. *EMBO J*, 4, 3031–7.

Virji, M., Kayhty, H., Ferguson, D. J., Alexandrescu, C., Heckels, J. E. and Moxon, E. R. (1991) The role of pili in the interactions of pathogenic *Neisseria* with cultured human endothelial cells. *Mol Microbiol*, 5, 1831–41.

Yanisch-Perron, C., Vieira, J. and Messing, J. (1985) Improved M13 phage cloning vectors and host strains: nucleotide sequences of the M13mp18 and pUC19 vectors. *Gene*, 33, 103–19.

We claim:

1. A method of preparing a composition, said composition comprising an isolated heterologous gene product and a pharmaceutically acceptable carrier, said method comprising the steps of:
   (a) inserting a gene coding for the heterologous gene product into an expression vector;
   (b) transforming said expression vector into a commensal *Neisseria*;
   (c) expressing said heterologous gene product in said commensal *Neisseria*;
   (d) isolating said heterologous gene product from the *Neisseria* of (c); and
   (e) combining the heterologous gene product of (d) with the pharmaceutically acceptable carrier, wherein said heterologous gene product is selected from (1) a product of a gene of a non-Neisserial organism and (2) a product of a gene of a pathogenic *Neisseria*.

2. The method of claim 1, wherein said commensal *Neisseria* is selected from the group consisting of *N. cinerea, N. lactamica, N. elongata, N. flava, N. flavescens, N. polysaccharea, N. sicca, N. mucosa, N. perflava* and *N. subflava*.

3. The method of claim 1, wherein the heterologous gene product is the product of a gene of a pathogenic *Neisseria*.

4. The method of claim 3, wherein the heterologous gene product is (a) transferrin binding protein; (b) a Cu,Zn—SOD; (c) an NspA; (d) a porin; (e) an outer membrane protein; or a fragment of any of (a)–(e).

5. The method of claim 1, wherein said isolating comprises:
   (i) suspending said commensal *Neisseria* cells in the presence of detergent;
   (ii) incubating the suspension;
   (iii) extracting a protein fraction from the cells; and
   (iv) isolating the heterologous gene product from the protein fraction.

6. The method of claim 5, wherein the protein fraction is of molecular weight 50 kDa or lower when measured by SDS-PAGE.

7. The method of claim 5, wherein the protein fraction is of molecular weight from 40 kDa to 90 kDa when measured by SDS-PAGE.

8. The method of claim 5, wherein the protein fraction is of molecular weight at least 80 kDa when measured by SDS-PAGE.

9. A method according to claim 1, wherein step (d) comprises (i) isolating outer membrane vesicles from the *Neisseria* of step (c), and (ii) isolating said heterologous gene product from said outer membrane vesicles; and wherein said heterologous gene product comprises an outer membrane protein or is directed to the outer membrane of said *Neisseria* by a signal sequence.

10. A composition obtained by the method of claim 9.

* * * * *

UNITED STATES PATENT AND TRADEMARK OFFICE
CERTIFICATE OF CORRECTION

PATENT NO. : 7,157,245 B2 Page 1 of 1
APPLICATION NO. : 09/942583
DATED : January 2, 2007
INVENTOR(S) : Robinson et al.

It is certified that error appears in the above-identified patent and that said Letters Patent is hereby corrected as shown below:

Title page, change item (73) Assignee to read as follows:

Health Protection Agency, Salisbury, Wiltshire (GB);

Imperial College Innovations Limited, London (GB)

Signed and Sealed this

Eighteenth Day of September, 2007

JON W. DUDAS
*Director of the United States Patent and Trademark Office*

SEQUENCE LISTING

```
<160> NUMBER OF SEQ ID NOS: 12

<210> SEQ ID NO 1
<211> LENGTH: 19
<212> TYPE: DNA
<213> ORGANISM: Unknown
<220> FEATURE:
<223> OTHER INFORMATION: PCR primer

<400> SEQUENCE: 1
gcagtctctc gagctcaag                                                19
```

```
<210> SEQ ID NO 2
<211> LENGTH: 19
<212> TYPE: DNA
<213> ORGANISM: Unknown
<220> FEATURE:
<223> OTHER INFORMATION: PCR PRIMER

<400> SEQUENCE: 2
cctctccact gacagaaaa                                              19

<210> SEQ ID NO 3
<211> LENGTH: 17
<212> TYPE: DNA
<213> ORGANISM: Unknown
<220> FEATURE:
<223> OTHER INFORMATION: PCR PRIMER

<400> SEQUENCE: 3
gtaaaacgac ggccagt                                                17

<210> SEQ ID NO 4
<211> LENGTH: 17
<212> TYPE: DNA
<213> ORGANISM: Unknown
<220> FEATURE:
<223> OTHER INFORMATION: PCR PRIMER

<400> SEQUENCE: 4
aacagctatg gaccatg                                                17

<210> SEQ ID NO 5
<211> LENGTH: 19
<212> TYPE: DNA
<213> ORGANISM: Unknown
<220> FEATURE:
<223> OTHER INFORMATION: SEQUENCING PRIMER

<400> SEQUENCE: 5
gcagtctctc gagctcaag                                              19

<210> SEQ ID NO 6
<211> LENGTH: 22
<212> TYPE: DNA
<213> ORGANISM: Unknown
<220> FEATURE:
<223> OTHER INFORMATION: SEQUENCING PRIMER

<400> SEQUENCE: 6
cgctttacac tttatgcttc cg                                          22

<210> SEQ ID NO 7
<211> LENGTH: 17
<212> TYPE: DNA
<213> ORGANISM: Unknown
<220> FEATURE:
<223> OTHER INFORMATION: SEQUENCING PRIMER

<400> SEQUENCE: 7
gtaaaacgac ggccagt                                                17

<210> SEQ ID NO 8
<211> LENGTH: 17
<212> TYPE: DNA
<213> ORGANISM: Unknown
<220> FEATURE:
```

```
<223> OTHER INFORMATION: SEQUENCING PRIMER

<400> SEQUENCE: 8
aacagctatg gaccatg                                                      17

<210> SEQ ID NO 9
<211> LENGTH: 76
<212> TYPE: DNA
<213> ORGANISM: Unknown
<220> FEATURE:
<223> OTHER INFORMATION: LINKER SEQUENCE
<221> NAME/KEY: misc_feature
<222> LOCATION: (1)..(5)
<223> OTHER INFORMATION: Bam HI restriction site
<221> NAME/KEY: misc_feature
<222> LOCATION: (75)..(76)
<223> OTHER INFORMATION: XbaI restriction site
<221> NAME/KEY: misc_feature
<222> LOCATION: (8)..(15)
<223> OTHER INFORMATION: NotI restriction site
<221> NAME/KEY: misc_feature
<222> LOCATION: (16)..(21)
<223> OTHER INFORMATION: SnaBI restriction site
<221> NAME/KEY: misc_feature
<222> LOCATION: (22)..(33)
<223> OTHER INFORMATION: NcoI restriction site
<221> NAME/KEY: misc_feature
<222> LOCATION: (34)..(39)
<223> OTHER INFORMATION: SmaI restriction site
<221> NAME/KEY: misc_feature
<222> LOCATION: (46)..(51)
<223> OTHER INFORMATION: PstI restriction site
<221> NAME/KEY: misc_feature
<222> LOCATION: (52)..(75)
<223> OTHER INFORMATION: neisserial uptake sequence

<400> SEQUENCE: 9
gatcccggcg gccgctacgt accatgggag ctgcccgggg tccagctgca ggccgtctga       60
atcatttcag acggct                                                       76

<210> SEQ ID NO 10
<211> LENGTH: 76
<212> TYPE: DNA
<213> ORGANISM: Unknown
<220> FEATURE:
<223> OTHER INFORMATION: COMPLIMENTARY SEQUENCE TO SEQ ID NO: 9

<400> SEQUENCE: 10
ggccgccggc gatgcatggt accctcgacg ggccccaggt cgacgtccgg cagacttagt       60
aaagtctgcc gagatc                                                       76

<210> SEQ ID NO 11
<211> LENGTH: 20
<212> TYPE: DNA
<213> ORGANISM: Unknown
<220> FEATURE:
<223> OTHER INFORMATION: artificial sequence, alternative 5' end

<400> SEQUENCE: 11
tttttggaga attgaccatg                                                   20

<210> SEQ ID NO 12
<211> LENGTH: 591
<212> TYPE: DNA
<213> ORGANISM: Unknown
<220> FEATURE:
<223> OTHER INFORMATION: ARTIFICIAL SEQUENCE COMPRISING EXPRESSION
      CASSETTE OF nspA
```

```
<400> SEQUENCE: 12
tgaccataaa ggaaccaaaa tatgaaaaaa gcacttgcca cactgattgc cctcgctctc        60
ccggccgccg cactggcgga aggcgcatcc tttacgtcca agccgatgcc gcacacgcaa       120
aagcctcaag ctctttaggt tctgccaaag gcttcagccc gcgcatctcc gcaggctacc       180
gcatcaacga cctccgcttc gccgtcgatt acacgcgcta caaaaactat aaagccccat       240
ccaccgattt caaactttac agcatcggcg cgtccgccat ttacgacttc gacacccaat       300
cgcccgtcaa accgtatctc ggcgcgcgct tgagcctcaa ccgcgcctcc gtcgacttgg       360
gcggcagcga cagcttcagc caaacctcca tcggcctcgg cgtattgacg ggcgtaagct       420
atgccgttac cccgaatgtc gatttggatg ccggctaccg ctacaactac atcggcaaag       480 tcaaacactgt caaaaacgtc cgttccggcg aactgtccgt cggcgtgcgc gtcaaattct      540
gatatgcgcc ttattctgca aaccgccgag ccttcggcgg ttttgttttc t                591
```